United States Patent [19]
Ries et al.

[11] Patent Number: 5,766,042
[45] Date of Patent: Jun. 16, 1998

[54] TOOL-LESS LOCKING AND SEALING ASSEMBLY FOR IMPLANTABLE MEDICAL DEVICE

[75] Inventors: Andrew J. Ries, Circle Pines; Thomas C. Bischoff, Minneapolis, both of Minn.

[73] Assignee: Medtronic, Inc., Minneapolis, Minn.

[21] Appl. No.: 579,959

[22] Filed: Dec. 28, 1995

[51] Int. Cl.$^6$ ............................ H01R 17/18; A61N 1/375
[52] U.S. Cl. ...................... 439/668; 439/349; 439/909; 128/419 P
[58] Field of Search .......................... 439/271, 296, 439/312, 345, 349, 371, 372, 668, 669, 909, 675; 128/419 P, 766, 784

[56] References Cited

U.S. PATENT DOCUMENTS

| | | | |
|---|---|---|---|
| 3,641,479 | 2/1972 | O'Brien et al. | 439/669 |
| 4,367,907 | 1/1983 | Buck | 439/669 |
| 4,540,236 | 9/1985 | Peers-Trevarton | 439/349 |
| 4,704,103 | 11/1987 | Stober et al. | 604/175 |
| 4,934,366 | 6/1990 | Truex et al. | 128/149 P |
| 5,070,605 | 12/1991 | Daglow et al. | 439/668 |
| 5,125,915 | 6/1992 | Berry et al. | 604/283 |
| 5,413,595 | 5/1995 | Stutz, Jr. | 607/637 |

*Primary Examiner*—Hien Vu
*Attorney, Agent, or Firm*—Reed A. Duthler; Harold R. Patton

[57] ABSTRACT

A connector assembly for effectuating electrical and mechanical coupling between an implantable device and a lead comprises a main body portion and a rotating lever which collectively define a socket for receiving the terminal end of the lead therein. When the lever is in an unlocked or open position, very little insertion force is required to introduce the terminal end of the lead into the socket. When the lever is rotated to its closed position, a J-groove connection between the lever and the main body portion causes the lever to be drawn toward the main body portion. This inward travel of the lever causes an annular sealing grommet in the connector assembly to be compressed around the circumference of the lead body, effectuating a frictional and fluid-tight connection between the lead and the implantable device. In another embodiment of the invention, compression of the sealing grommet is accomplished by pressing downward on a slide element. Complementary stepped-ramp bosses or protrusions on the slide element and main body of the connector assembly are such that as the slide element travels downward, it is simultaneously pulled inward slightly to compress the sealing grommet.

4 Claims, 26 Drawing Sheets

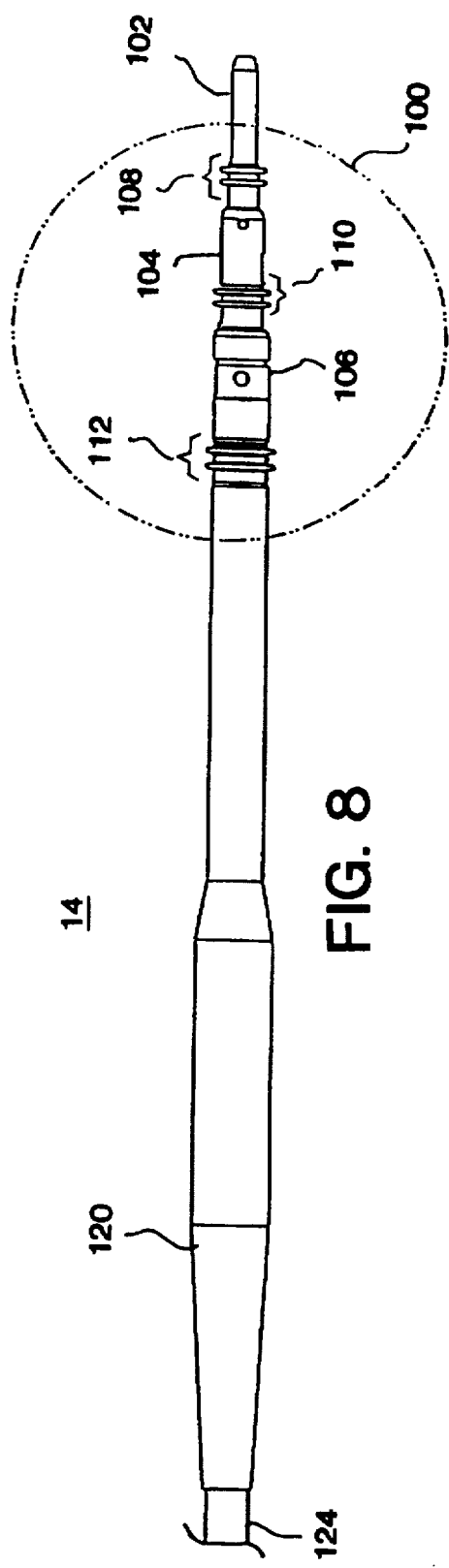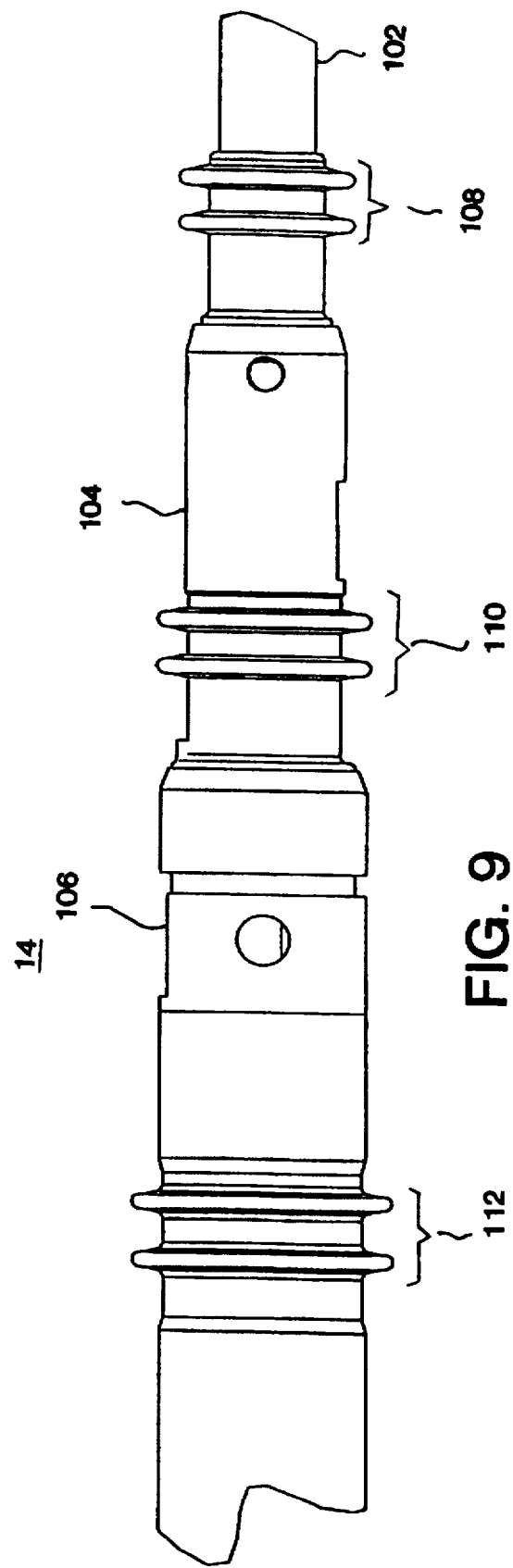
FIG. 8
FIG. 9

1

TOOL-LESS LOCKING AND SEALING ASSEMBLY FOR IMPLANTABLE MEDICAL DEVICE

FIELD OF THE INVENTION

The present invention relates generally to automatic, body-implantable medical device systems, and more particularly relates to a lead locking and sealing assembly for an implantable medical device.

BACKGROUND OF THE INVENTION

Various types of electronic devices are known for which an electrical and mechanical connection must be established between a wire or other flexible conductor and an electronic component. For example, there are numerous classes of automatic, body-implantable medical device systems, such as cardiac pacemakers and defibrillators, neural stimulators, and the like, for which it is commonly necessary to establish an electrical and mechanical coupling between an insulated conductive lead and an electronic component of the system. In a typical implantable pacemaker system, one or more pacing and sensing leads are coupled at their proximal ends to a hermetically enclosed pulse generator and have their distal ends disposed in or around the patient's heart. The leads function to conduct electrical cardiac signals to sensing circuitry within the hermetic enclosure, and to convey stimulating pulses from the pulse generator to the patient's heart.

There are particularly stringent design criteria with regard to the mechanical and electrical properties of the connection between a lead and a body-implantable device. An implantable device's lead connection is preferably highly reliable, both from a mechanical and from an electrical point of view, due to the potentially serious medical implications of either mechanical or electrical failure of the lead connection. Also, any physical structure used to implement an implantable device lead connection must be biologically inert (i.e., biocompatible), and is preferably small and light-weight.

In addition, a lead connection should be capable of withstanding repeated flexing of the lead with respect to the device itself. This consideration is one reason that implantable leads are often implemented as a coiled conductor within an elongate insulative sleeve of silicone rubber, polyurethane, or the like. Such a coiled conductor configuration has been shown in the prior art to have desirable fatigue resistant characteristics. Also, a lead connection should be strong enough to resist unintended disconnection due to the various forces that may be exerted upon it throughout the time it is implanted in the human body. At the same time, however, the delicate surgical process associated with implantation of such devices makes it desirable that the lead connection be relatively simple to effectuate in the surgical environment.

Implantable devices such as pacemakers are typically battery-powered electronic devices which are susceptible to breakage, failure, or battery depletion. Thus, such devices may occasionally need to be explanted and/or replaced. Often, though, the lead associated with the device need not be extracted along with the device. The previously implanted lead may be functioning properly, and in some cases may have become ingrown within body tissue, making lead removal undesirable. Consequently, a further preferable feature of a lead connection for an implantable device is that it should allow for disconnection without damage either to the lead or to the device, in order that the device may be removed and/or replaced without extraction of the lead.

One prevalent means in the prior art for establishing the electrical and mechanical connection between a lead and an implantable pulse generator has been to provide a connector assembly with molded-in connector blocks containing set-screws. A terminal pin provided at the terminal (proximal) end of the lead is received within a terminal receptacle in the connector, and the lead is then secured in place by tightening the set-screws. Those of ordinary skill in the art will appreciate that in some cases, the set-screws provide the requisite electrical contact between the lead conductor and the pacemaker's hermetic feedthrough elements.

With conventional connector and set-screw lead connecting arrangements, proper tightening of the set-screws can be of critical importance. Over-torquing of a set-screw can cause stripping of the set-screw threads or damage to the lead terminal or lead conductor. On the other hand, under-torquing of a set-screw can lead to post-implant problems, since the lead may become disengaged from the connector receptacle. To address these issues, in some cases a specially-designed set-screw driver or other tool may be provided as a means to ensure proper tightening. For instance, the tool may be designed to "break away" or flex after a proper amount of torque has been applied to the set-screw.

A further consideration with set-screw lead connector arrangements is that after tightening, the set-screw must be sealed from body fluids and the harsh in vivo environment, to prevent corrosion or short-circuiting of the connector blocks or feedthrough elements. Such sealing is often accomplished using a set of grommets, which can be damaged during the tightening of the set-screws.

Numerous other techniques have been proposed in the prior art for establishing the electrical and mechanical connection between a lead to an implantable device. Several techniques are briefly described in U.S. Pat. No. 4,540,236 to Peers-Travarton, entitled "Quick Lock/Quick Release Connector," which patent is hereby incorporated by reference herein in its entirety.

SUMMARY OF THE INVENTION

In view of the foregoing and other considerations in relation to connector assemblies, the present invention is directed to connector assembly which requires no tools to accomplish lead connection and disconnection.

In one embodiment of the invention, a connector assembly has a main body portion and a rotating lever which together define a socket for receiving the proximal terminal assembly of an implantable device lead. In this embodiment, very little insertion force is necessary to introduce the lead's terminal assembly into the socket, when the rotating lever is in its open position. To make the secure electrical and mechanical connection, the rotating lever is rotated down to its locked position. Cams on the rotating lever are engaged within a "J-groove" formed in the main body portion of the connector assembly, such that rotation of the lever to the locked position causes a portion of the lever to be drawn in towards the main body portion. This inward travel causes a sealing grommet in the connector assembly to be compressed around the circumference of the lead body.

In another embodiment of the invention, a connector assembly is provided with one or more slides which are movable up and down with respect to a main body portion of the connector. The slide and main body are each provided with complementary stepped-ramp bosses thereon, such that as the slide is pressed down from an open position to a closed position, it is simultaneously drawn inward toward the main body portion. This inward travel causes compression of a sealing grommet around the circumference of a lead body inserted into the socket defined by the slide and the main body portion.

BRIEF DESCRIPTION OF THE DRAWINGS

Numerous features of the present invention will perhaps be best appreciated with reference to a detailed description of specific embodiments of the invention, which follows, when read in conjunction with accompanying drawings, wherein:

FIG. 8 is a side view of the proximal end of a lead adapted to be inserted into the connector assembly of FIGS. 7a and 7b;

FIG. 9 is a side view of a portion of the lead shown in FIG. 8;

DETAILED DESCRIPTION OF SPECIFIC EMBODIMENTS OF THE INVENTION

Figure 1:
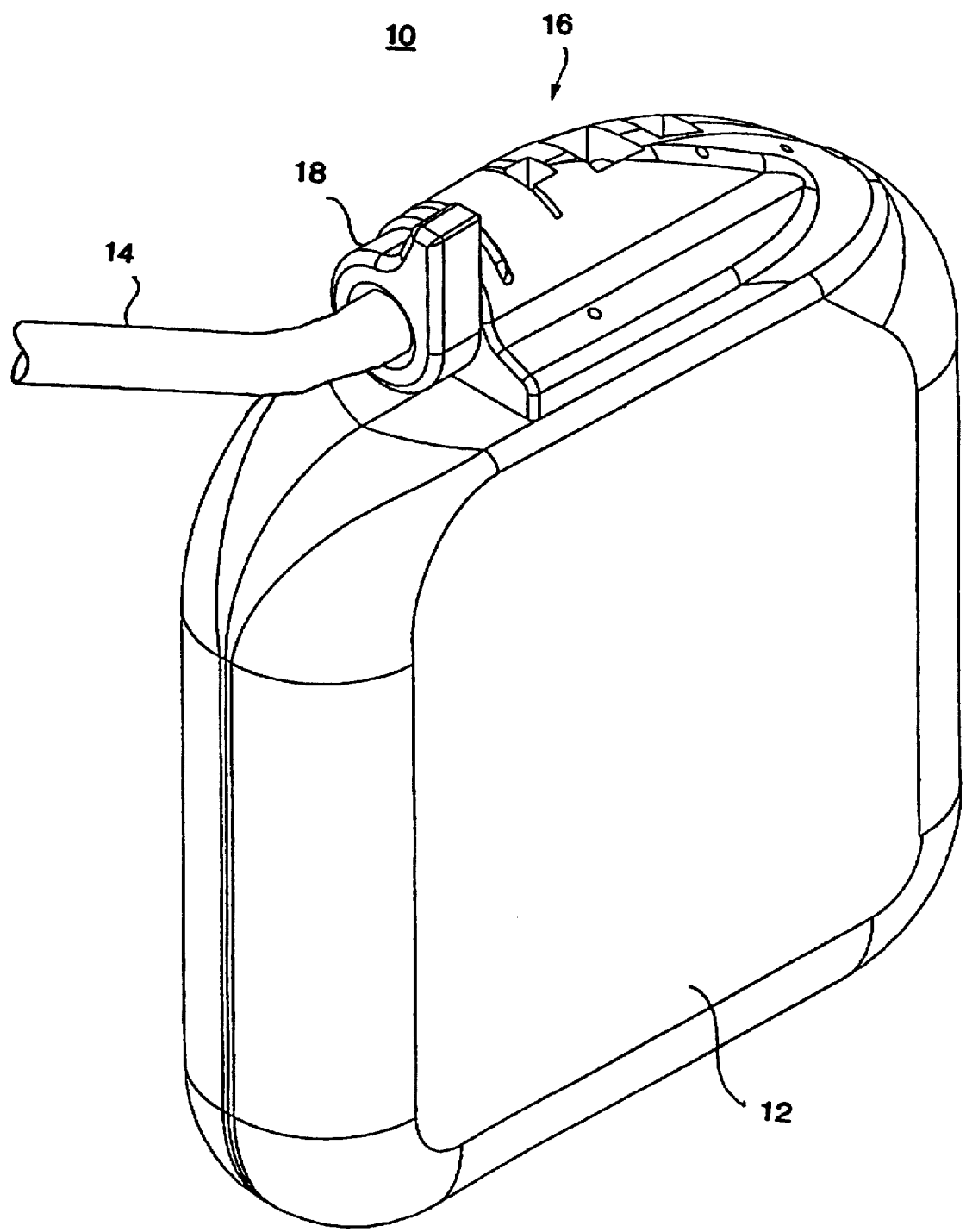
FIG. 1 is a perspective view of an implantable device system incorporating a tool-less connector assembly in accordance with one embodiment of the invention.

Referring to FIG. 1, there is shown a perspective view of a body-implantable medical device system 10 in accordance with one embodiment of the invention. System 10 as shown in FIG. 1 includes a pulse generator enclosure 12, an elongate pacing sensing lead 14 (only a proximal portion thereof being shown in FIG. 1), and a connector assembly 16 for establishing electrical and mechanical connection between pulse generator 12 and lead 14.

Although the present invention will be described herein in the context of an implantable pacemaker system 10, it is believed that those of ordinary skill in the art having the benefit of this disclosure will readily appreciate how the invention can be advantageously practiced in connection with numerous other types of electronic systems, including other implantable medical device systems such as cardioverters, defibrillators, and the like.

In accordance with one aspect the presently disclosed embodiment of the invention, no tools are necessary to facilitate connection between lead 14 and pulse generator 12. Instead, connector assembly 16 is actuated through rotation of a lever 18, which is shown in its "open" position in FIG. 1, and which is shown in its "closed" position in FIG. 2.

Figure 2:
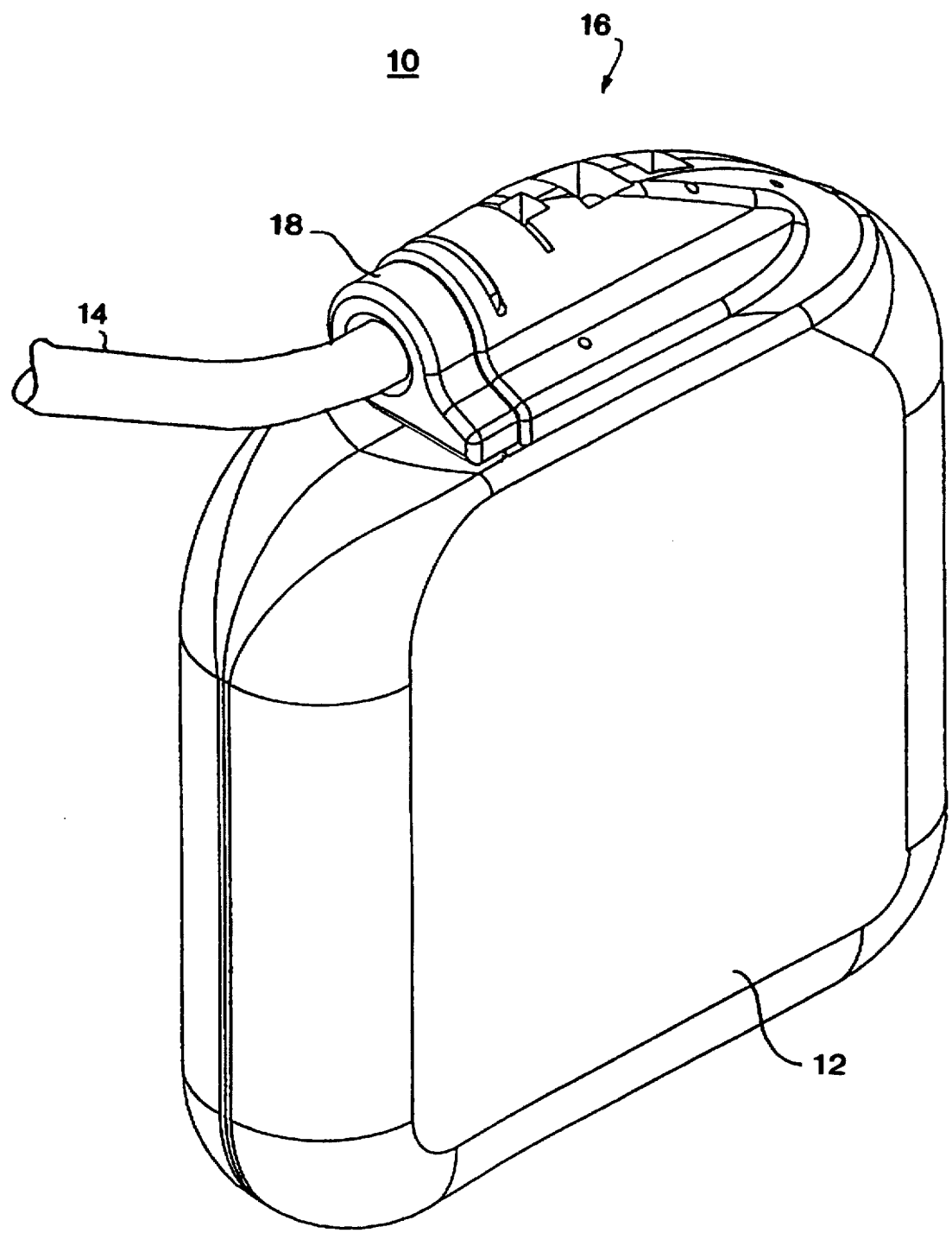
FIG. 2 is a perspective view of the implantable device system from FIG. 1 showing the connector assembly in a closed or locked position.
Figure 3:
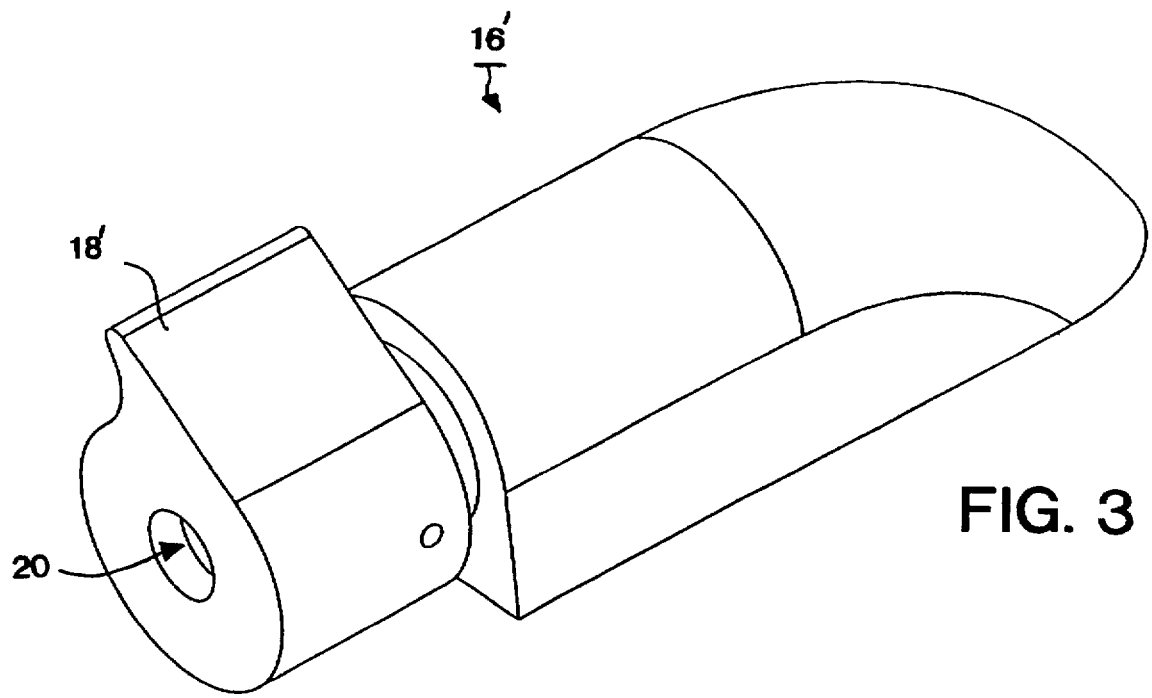
FIG. 3 is a perspective view of a connector assembly in accordance with another embodiment of the invention similar to that shown in FIGS. 1 and 2, the connector assembly of FIG. 3 being shown in an open position.
Figure 4:
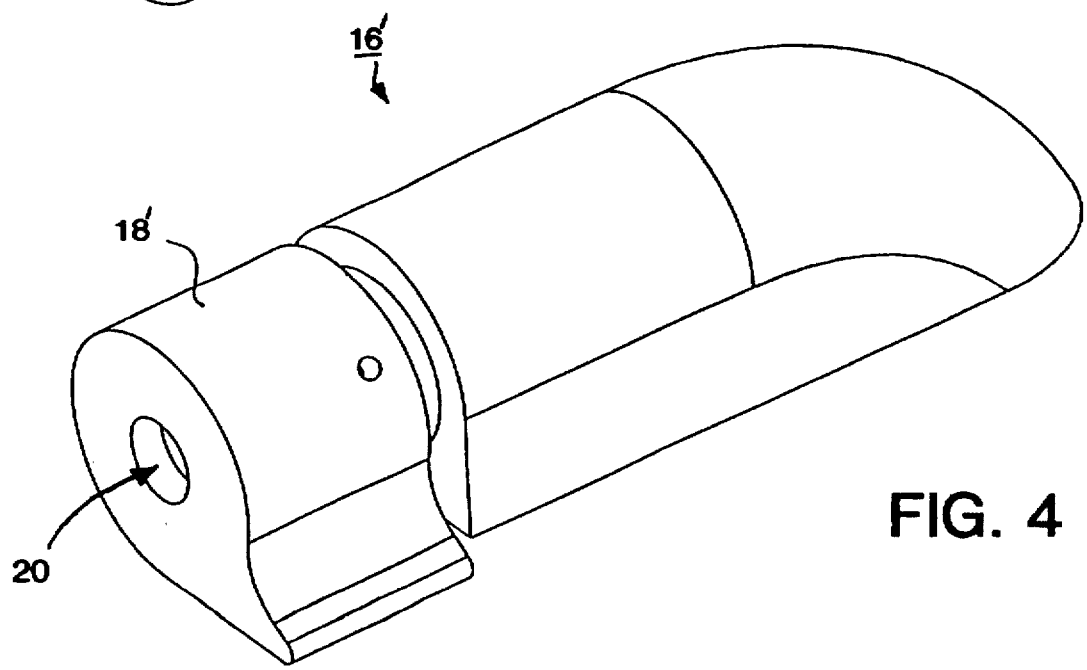
FIG. 4 is a perspective view of the connector assembly from FIG. 3, shown in FIG. 4 in a closed position.

FIGS. 3 and 4 similarly depict a connector assembly 16' that is substantially similar to that of FIGS. 1 and 2, with rotating lever 18' in its open and closed positions, respectively. (It is to be understood throughout this specification that those elements that are identical or substantially identical in more than one figure will retain identical reference numerals in those figures; primed notation, e.g., 16, 16', etc. ... will be used to indicate elements in various figures that may not be identical but are merely variants of one another.)

As shown in FIGS. 3 and 4, connector assembly 16' defines a socket 20 which extends through rotating lever 18' and which is adapted to receive the terminal (proximal) end of pacing/sensing lead 14 (not shown in FIGS. 3 and 4) therein.

Figure 5:
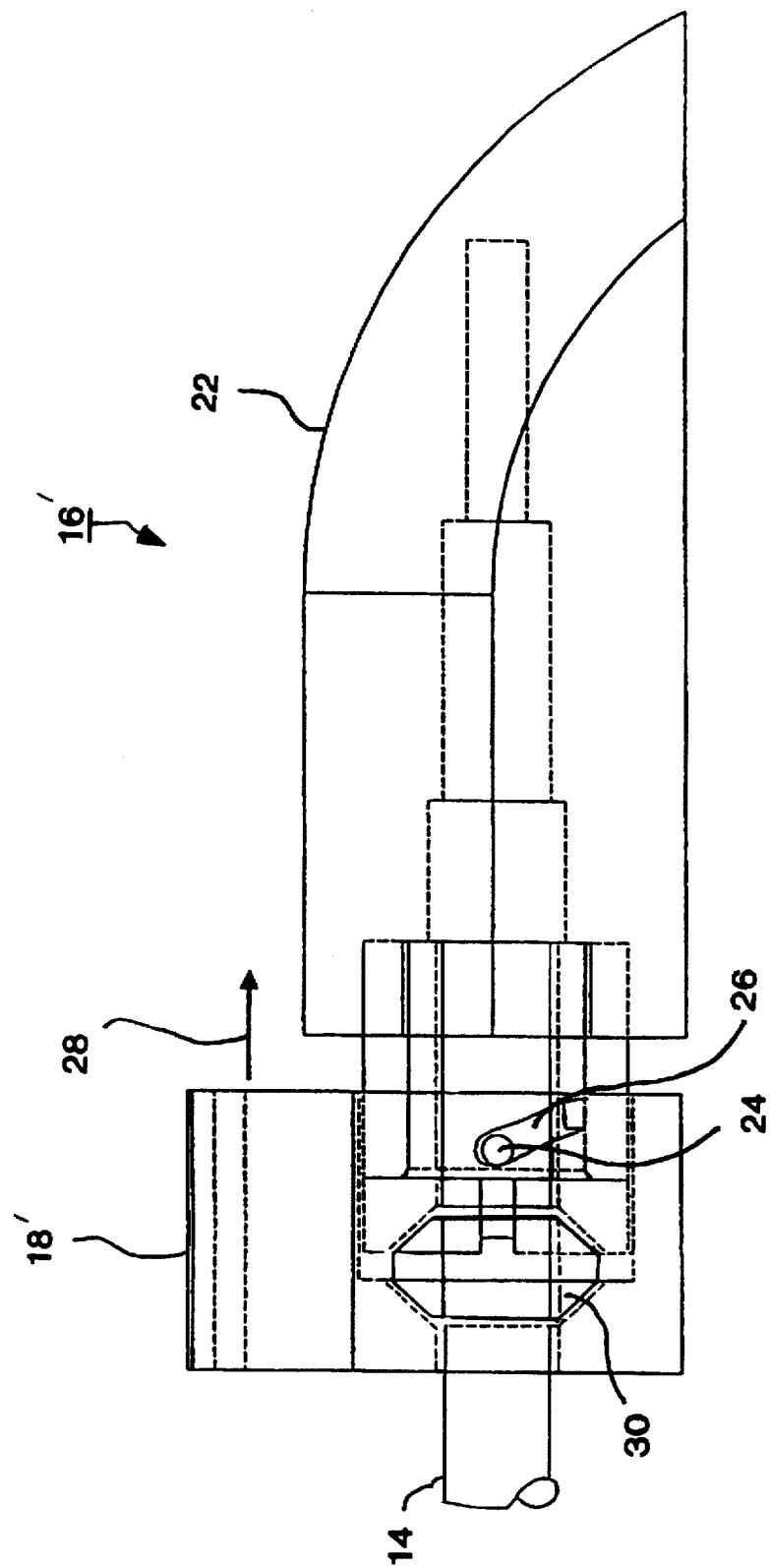
FIG. 5 ;a side cross-sectional view of the connector assembly from FIGS. 3 and 4.

In the presently disclosed embodiment of the invention, the terminal end of lead 14 is secured within connector assembly 16 (or 16') by compression force applied when lever 18 (or 18') is rotated into its closed position. This can perhaps be better appreciated with reference to the cross-sectional view of the embodiment of the invention from FIGS. 3 and 4, shown in FIG. 5. In FIG. 5, lever 18' is shown in the open position. Lever 18' is coupled to a main body portion 22 of connector assembly 16' via a conventional cam and J-groove arrangement (i.e., with a cam 24 engaged within a J-shaped groove 26), such that rotation of lever 18' causes lever 18' to be drawn toward main body portion 22, in the direction of arrow 28 in FIG. 5. (Alternatively, lever 18' can be threadably engaged to main body portion 22, with the pitch of the threads being sufficient to draw lever 18 toward main body portion 22 upon rotation or "screwing in") of lever 18' from its open to its closed position.) A compressible (e.g., rubber) sealing grommet 30 is disposed between main body portion 22 and lever 18' , such that the inward travel of lever 18' upon rotation of lever 18' causes grommet 30 to be compressed. This tightens grommet 30 around lead body 14, thereby effectuating a frictional and fluid-tight seal which prevents lead body 14 from being withdrawn from connector assembly 16' and which acts as a barrier against seepage of fluids into connector assembly 16'.

Figure 6:
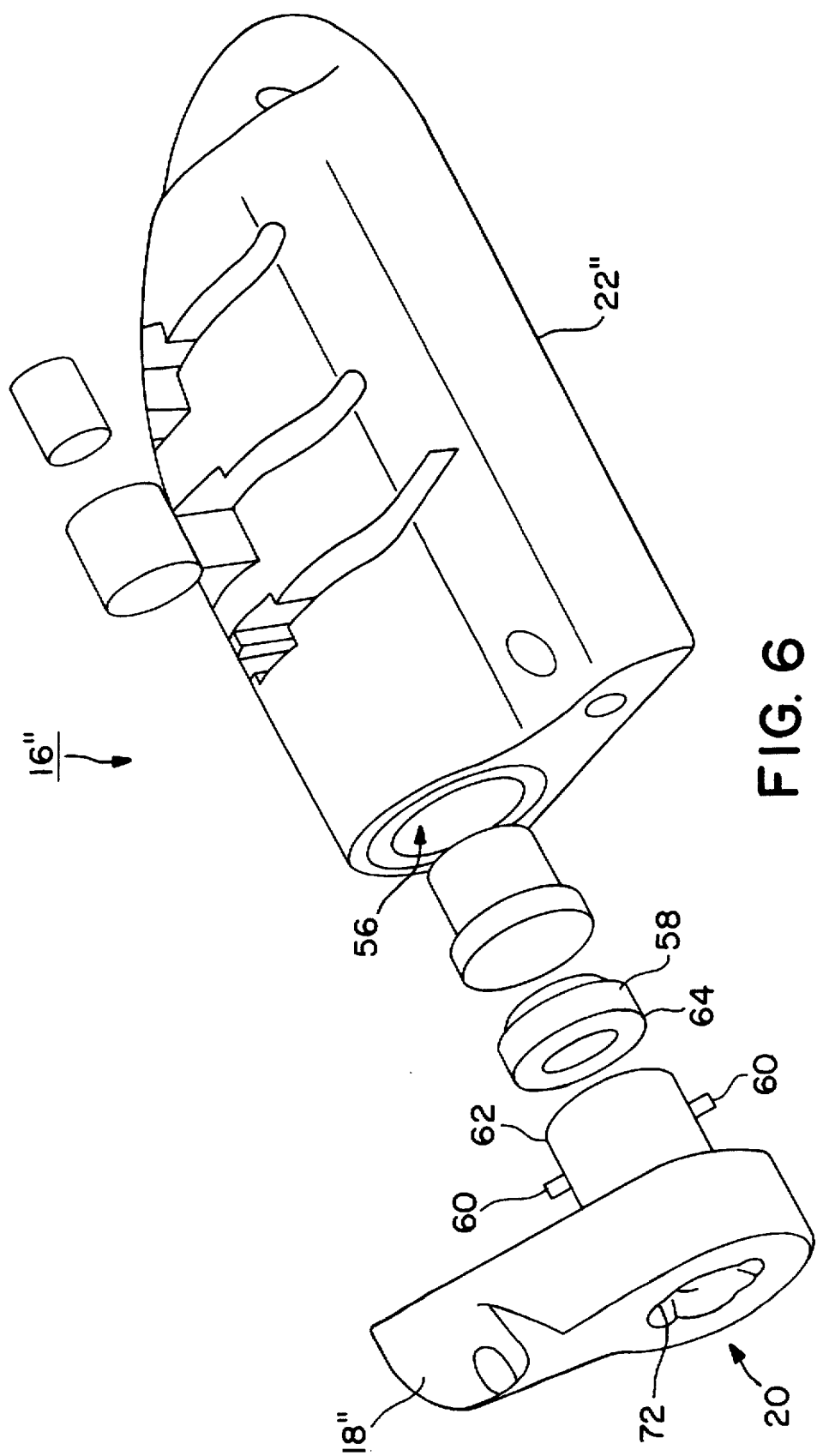
FIG. 6 is an exploded perspective view of a tool-less connector assembly in accordance with another embodiment of the invention.

FIG. 6 is an exploded perspective view of a connector assembly 16" in accordance with a another alternative embodiment of the invention. Connector assembly 16" operates in substantially the same manner as the connector assemblies 16 and 16' described above with reference to FIGS. 1–5, but differs slightly from connector assemblies 16' and 16" in its internal configuration of sealing grommets and the like, as will be hereinafter described in further detail.

Like connector assembly 16', connector assembly 16" in FIG. 6 consists of a main body portion 22" and a lever 18" which rotates from an open or unlocked position (shown in FIG. 6) to a closed or locked position. Main body portion 22" and lever 18" define a socket 20 into which the terminal (proximal) end of a lead is inserted.

When the terminal (proximal) end of a lead (not shown in FIG. 6) is inserted into socket 20, rotating lever 18" causes a rubber sealing grommet 58 to be compressed around the lead body, thereby securing the lead in connector assembly 16". This compression is accomplished as a result of the engagement of cams 60 on lever 18" in J-shaped grooves (not visible in the view of FIG. 6) formed in the portion of socket 20 defined by main body portion 22". (Again, in an alternative embodiment, lever 18" is threadably coupled to main body). As in the embodiments of FIGS. 1–5, in the embodiment of FIG. 6 rotation of lever 18" into its closed position causes a plunger portion 62 of lever 18" to be drawn inward into main body portion 22". As plunger 62 travels into main body portion 22", it compresses grommet 58 around the circumference of the lead body.

Main body portion 22" and lever 18" of the embodiment of FIG. 6 are preferably made of molded polyurethane or another suitably rigid and biocompatible material. Plunger portion 62 of lever 18" may be made of metal, for example 316L stainless steel or the like. Sealing grommet 58 is preferably made of an elastomeric material, such as low-durometer silicone rubber or the like. A thrust washer 64 may be provided to prevent rotation of lever 54 (and hence, of plunger 62) from damaging sealing grommet 58. Thrust washer 64 may be made of polyurethane or metal, for example.

Figure 7A:
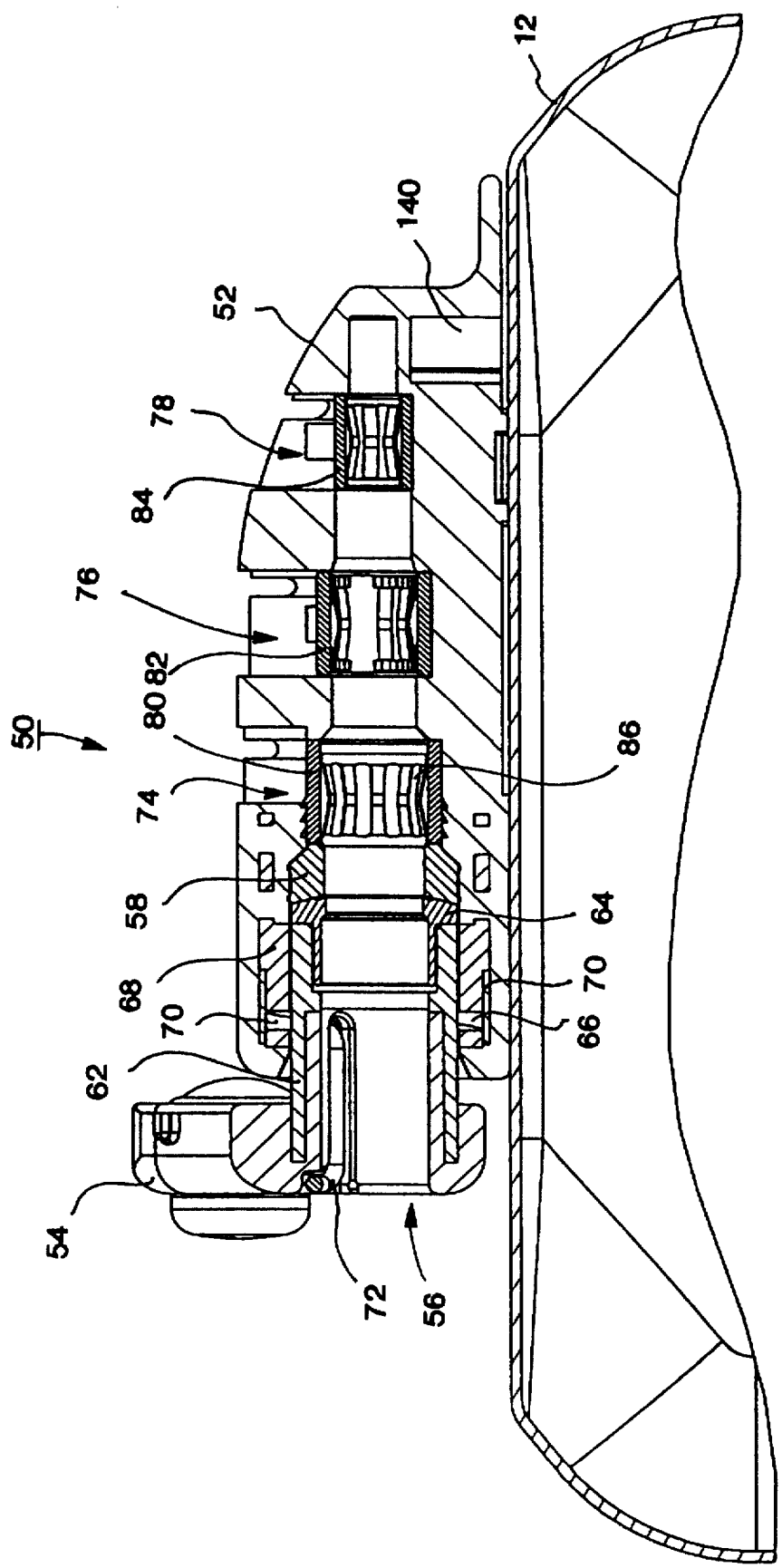
FIGS. 7a and 7b are side cross-sectional views of a connector assembly in accordance with still another embodiment of the invention, showing the connector assembly in open and closed positions, respectively.
Figure 7B:
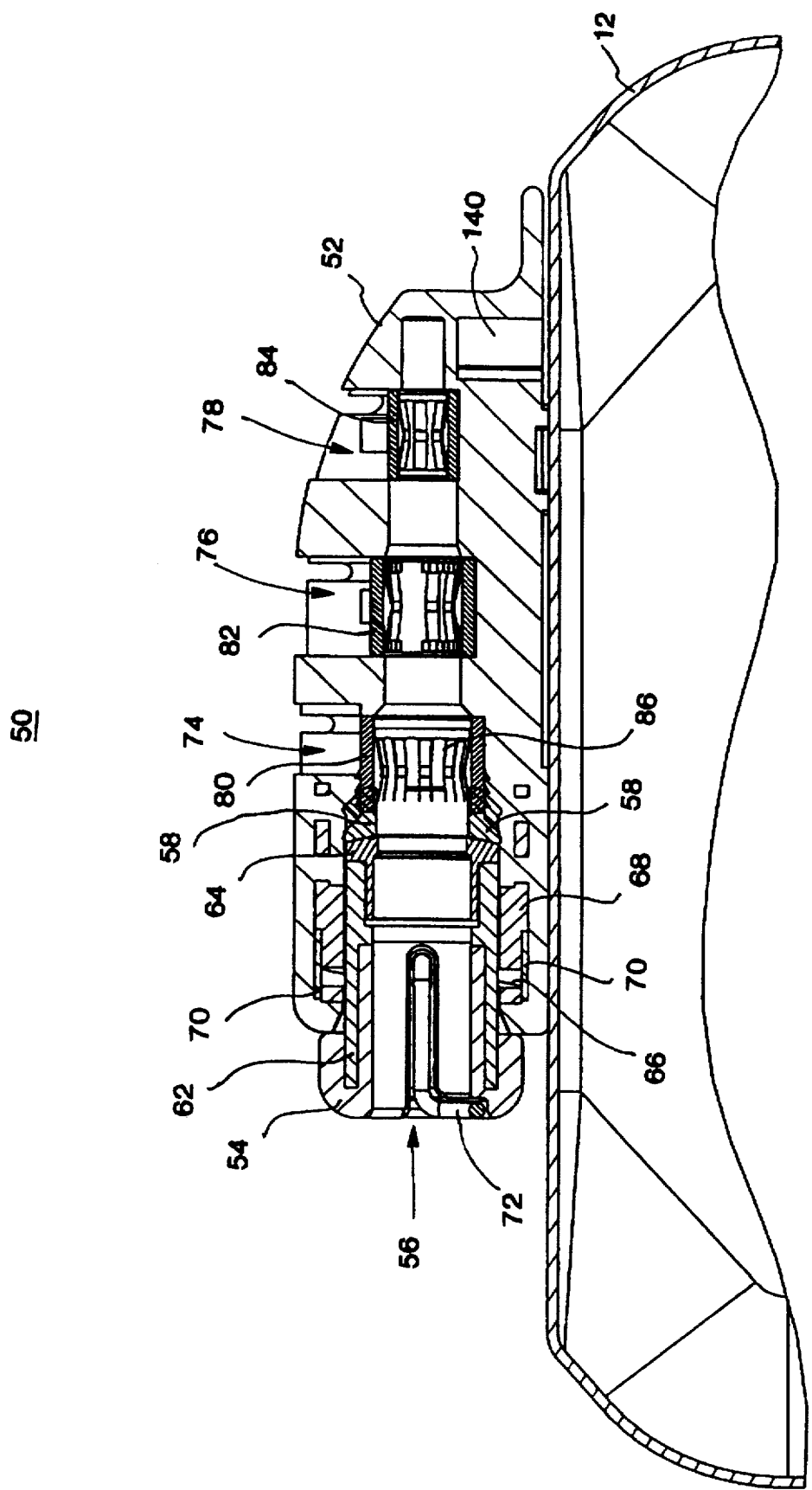

Cross-sectional views of still another alternative embodiment of the invention are provided in FIGS. 7a and 7b, which show a connector assembly 50 in open and closed positions, respectively. In FIG. 7b, lever 54 is shown in its closed or locked position, such that plunger 62 is drawn into main body portion 52, thereby compressing thrust washer against sealing grommet 58.

As noted above, main body portion 52 is preferably made of molded polyurethane. To facilitate formation of a J-groove in socket 56, (the J-groove being designated with reference numeral 66 in FIGS. 7a and 7b), an insert assembly including a stainless steel or titanium sleeve 68 is molded into main body 52. A tubular cover 70 is fitted over sleeve 68 to prevent polyurethane from filling in J-groove 66 during the molding process. From FIGS. 7a and 7b, it is also apparent that cams 60 are actually the ends of a generally folded U-shaped spring clip 72, which ends project through corresponding holes in plunger 62. This implementation advantageously simplifies manufacturing and assembly of connector assembly 50, as spring clip 72 can be compressed during the manufacturing process to facilitate insertion of cams 60 into J-groove 66. Once cams 60 are engaged in J-groove 66, lever 54 is prevented from detaching from main body 52.

The embodiments of the invention thus far described are adapted to function as a tripolar connectors, i.e., connectors for a lead having three separate, mutually isolated conductors therein. It is to be understood that the present invention is not limited to tripolar connector assemblies, however, and it is believed that those of ordinary skill in the art having the benefit of the present disclosure will be readily able to practice the invention in the context of connector assemblies for leads having more or less than three conductors therein.

To facilitate the three electrical connections necessary for a tripolar lead, three contact assemblies, designated generally with reference numerals 74, 76, and 78 in FIG. 7a and 7b, are provided in connector assembly 50. Contact assemblies 74, 76, and 78 each comprise an outer metal (e.g., 316L stainless steel) ferrule 80, 82, and 84, respectively, and an inner "multi-beam" contact, a typical one of which in contact assembly 74 being designated with reference numeral 86. Each multibeam contact in contact assemblies 74, 76, and 78 is adapted to make electrical contact with a separate ring electrode disposed on the terminal or proximal end of the lead (not shown in FIGS. 7a and 7b).

Of course, any connector block system should effectuate not only a mechanical connection between the lead and the pulse generator, but also one or more electrical connections therebetween. In the presently disclosed embodiment of the invention, lead 14 has a tripolar configuration, meaning that it has three separately insulated conductors extending along its length.

FIGS. 8 and 9 are side views of the proximal or terminal end of lead 14 adapted for use with the connector block assembly 50 in accordance with the presently disclosed embodiment of the invention. FIG. 9 is an enlarged side view of the portion of the proximal end of lead 14 contained within the dashed line designated 100 in FIG. 8. Although lead 14 is a tripolar lead, it is contemplated that the present invention may be advantageously practiced in the context of leads having more or fewer conductors therein, and it is believed that those of ordinary skill in the art having the benefit of the present disclosure will be readily able to do so.

As shown in FIGS. 8 and 9, lead 14 includes three distal electrical contacts or connector electrodes, designated with reference numerals 102, 104, and 106, with connector electrode 102 being a pin electrode on the proximal end of lead 14, and electrodes 104 and 106 being ring electrodes spaced distally away from the proximal end. In the preferred embodiment, electrodes 102, 104, and 106 are made of stainless steel or another suitably conductive and biostable material.

Interspersed with electrodes 102, 104, and 106 are three sets of sealing rings 108, 110, and 112, which function to further provide a fluid-tight seal between the terminal end of lead 14 and connector block assembly 50. Sealing rings 108, 110, and 112 are preferably made of silicone rubber, polyurethane, or the like.

Figure 10:
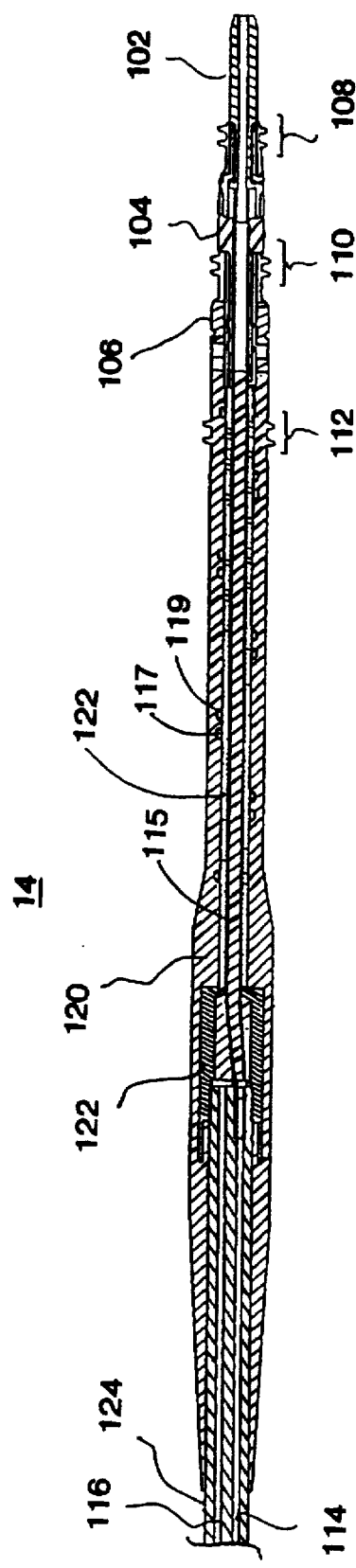
FIG. 10 is a side cross-sectional view of the proximal end of the lead from FIG. 8.
Figure 11:
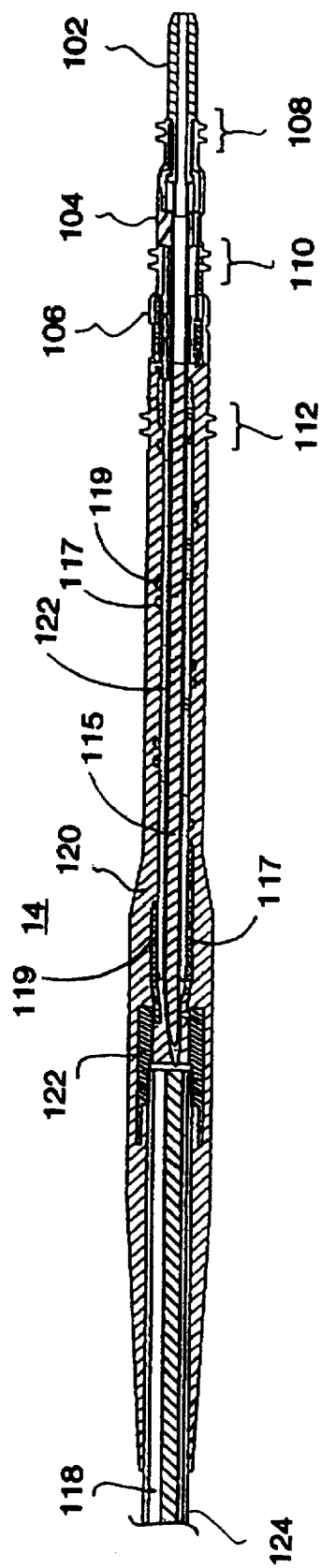
FIG. 11 is another side cross-sectional view of the proximal end of the lead from FIG. 8.
Figure 12:
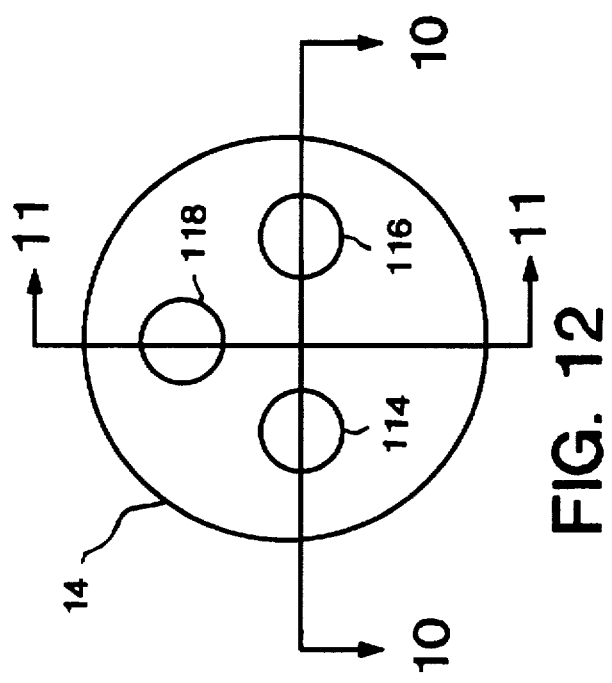
FIG. 12 is an end cross-sectional view of the lead from FIG. 8 showing the orientation of the cross-sections of FIGS. 11 and 12.

The proximal or terminal end of lead 14 is also depicted in the more detailed cross-sectional views of FIGS. 10 and 11. Lead 14 in accordance with the presently disclosed embodiment is a triaxial, multilumen lead, as shown in the cross-sectional view of FIG. 12, which also indicates the orientation of the cross-sections in FIGS. 10 and 11. In particular, lead 14 has three internal lumens 114, 116, and 118. These three lumens enable three separate conductors to extend along the length of lead 14.

Figure 13:
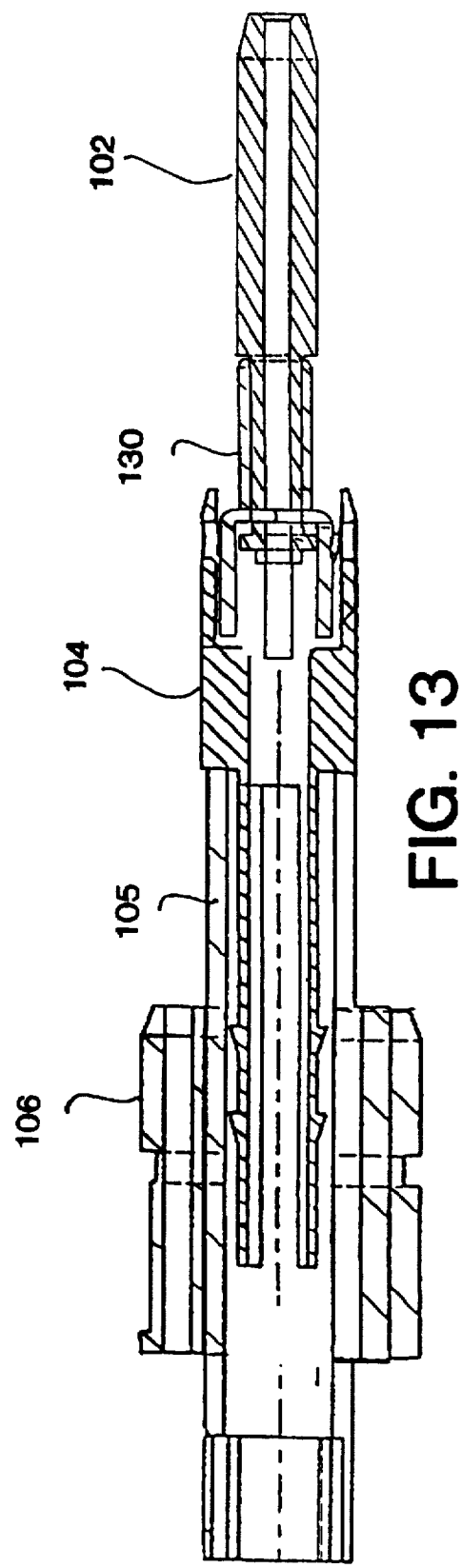
FIG. 13 is a side cross-sectional view of individual components of the terminal assembly of the lead from FIG. 8.

FIG. 13 shows the various components which comprise the terminal end of lead 14. For clarity, the outer insulative sheath of lead 14, which is designated with reference numeral 120 in FIGS. 10 and 11 and preferably made of polyurethane or the like, is not shown in FIG. 13. As shown in FIGS. 10 and 11, the terminal end of lead 14 includes a connector sleeve stiffener 122, which in the preferred embodiment is made of molded 55D polyurethane. Stiffener 122 is coupled at its distal end to the multi-lumen body of lead 14, designated with reference numeral 124 in the Figures. At is proximal end, stiffener 122 is bonded to the distal end of a polyurethane ring electrode liner 105, which is shown in FIG. 13. Liner 105 functions to insulate ring electrode 106 from ring electrode 104, which is press-fit inside liner 105. Snap-fit into the proximal end of ring electrode 104 is a molded polyurethane insert 130. Pin electrode 102, in turn, is snap-fit into insert 130.

Figure 14:
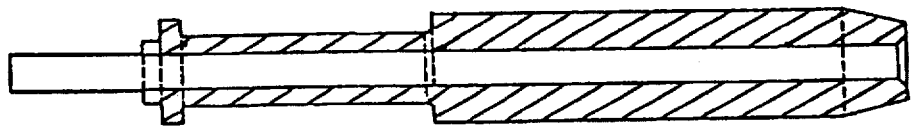
FIG. 14 is a side cross-sectional view of the pin electrode from the lead of FIG. 8.
Figure 15A:
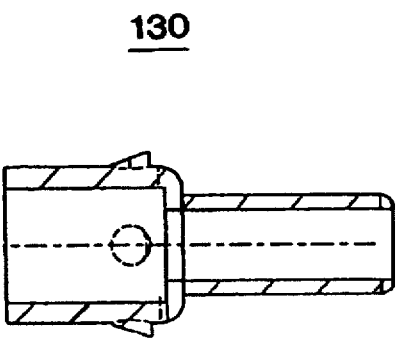
FIGS. 15a and 15b are side and end cross-sectional views, respectively, of a sense ring insert component of the lead of FIG. 8.
Figure 15B:
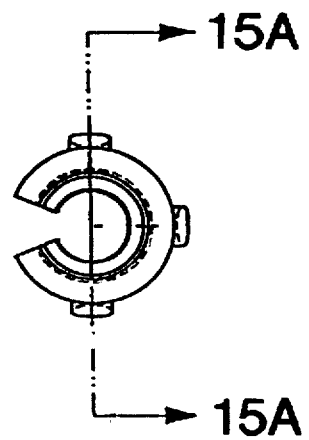
Figure 16A:
FIGS. 16a and 16b, are side cross-sectional views of a ring connector electrode from the lead of FIG. 8.
Figure 16B:
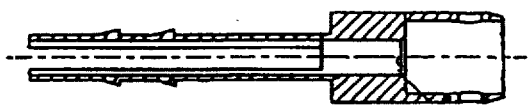
Figure 17A:
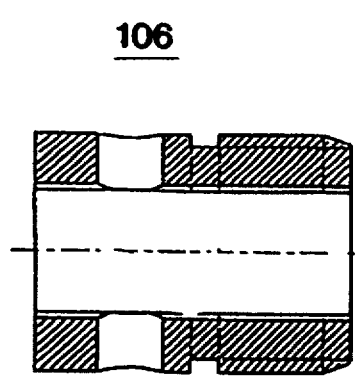
FIGS. 17a, 17b, 17c, and 17d are side cross-sectional, end cross-sectional, side cross-sectional and end cross-sectional views of another ring connector electrode from the lead of FIG. 8.
Figure 17B:
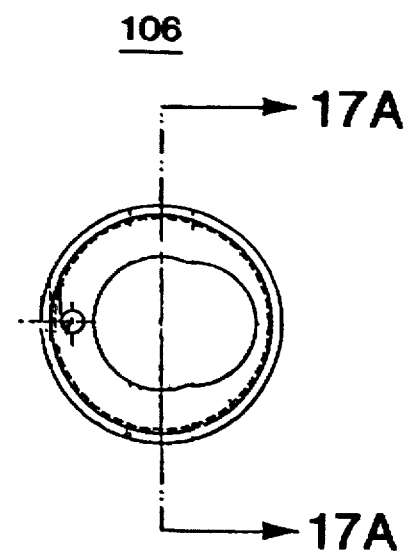
Figure 17C:
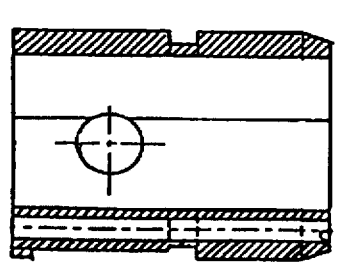
Figure 17D:
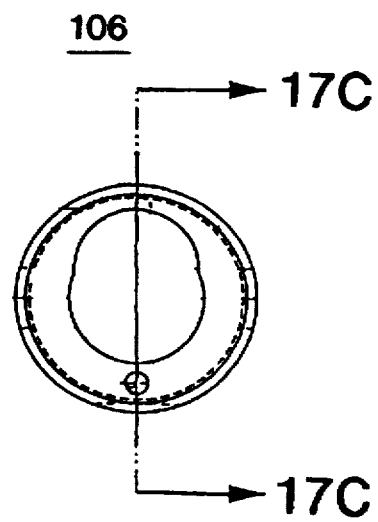
Figure 18A:
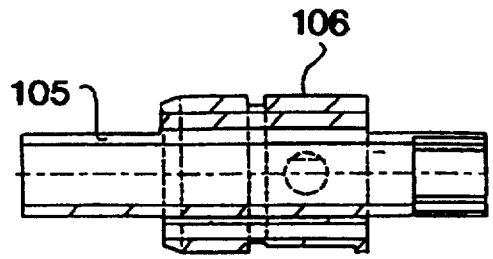
FIGS. 18a, 18b, 18c, and 18d are side cross-sectional, end cross-sectional, side cross-sectional and end cross-sectional views of a ring connector electrode assembly from the lead of FIG. 8, including the ring connector electrode from FIGS. 17a, 17b, 17c, and 17d.
Figure 18B:
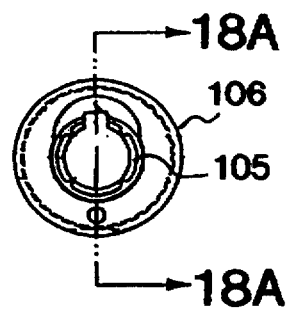
Figure 18C:
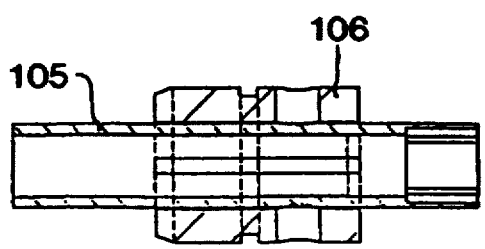
Figure 18D:
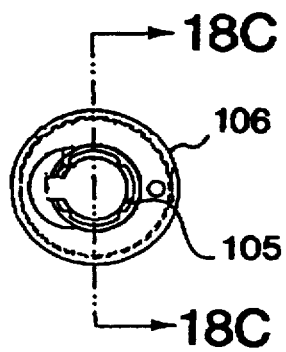
Figure 19:
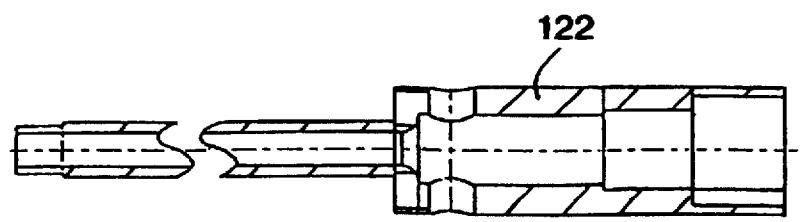
FIG. 19 is a side cross-sectional view of a stiffener component from the lead of FIG. 8.

The various components of the terminal end of lead 14—insert 130, ring electrode 104, sleeve 105, ring electrode 106 and stiffener 122—are shown in more detail in FIG. 14 (pin electrode 102), FIGS. 15a and 15b (side and end views, respectively, of insert 130), FIGS. 16a and 16b (cross-sectional views of ring electrode 104), FIGS. 17a, 17b, 17c, and 17d (side, end, side, and end cross-sectional views, respectively, of ring electrode 106), FIGS. 18a, 18b, 18c, and 18d (side, end, side, and end cross-sectional views, respectively, of the ring electrode assembly comprising ring electrode 106 and liner 105), and FIG. 19 (stiffener 122)

Figure 20A:
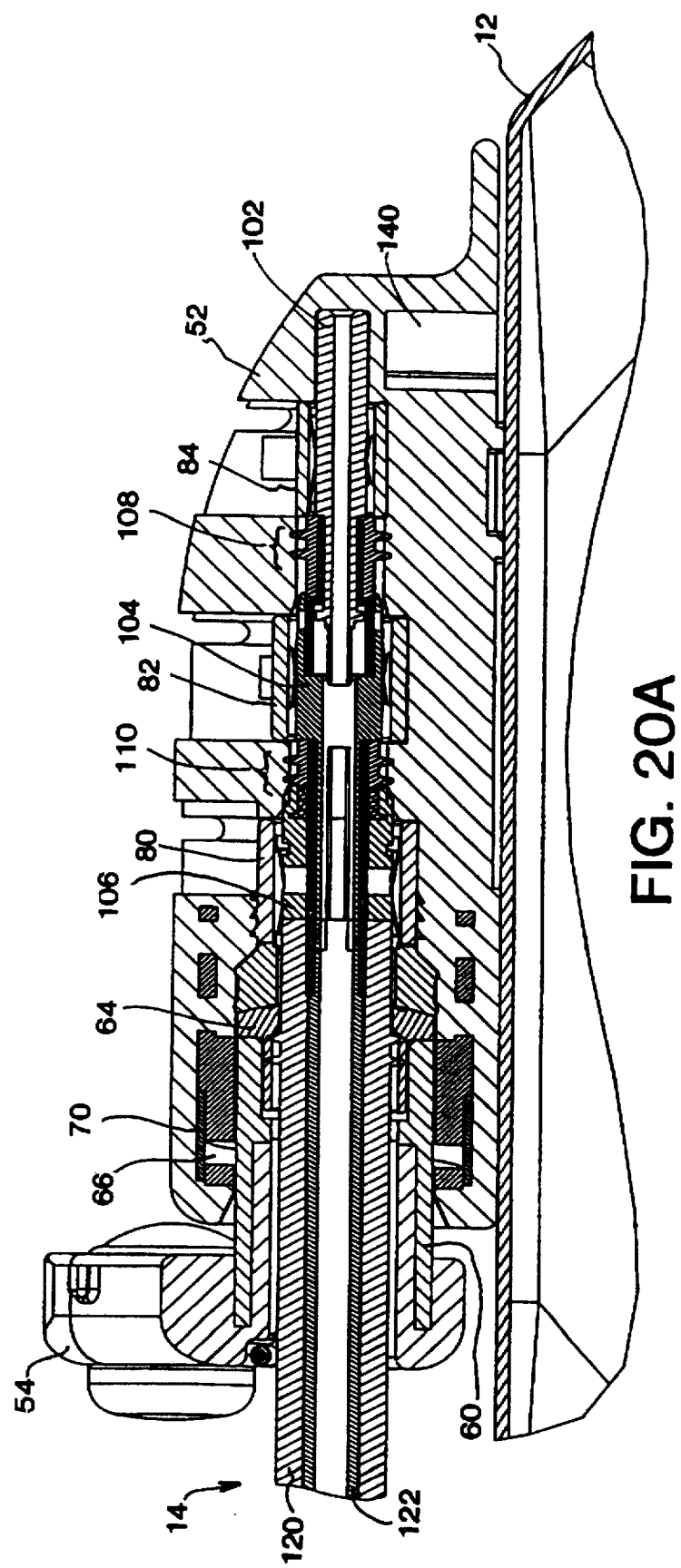
FIGS. 20a and 20b are side cross-sectional views of the connector assembly of FIGS. 7a and 7b showing a lead similar to that described with reference to FIG. 8 inserted therein, with FIG. 20a showing the connector assembly in an open position and FIG. 20b showing the connector assembly in a closed position.
Figure 20B:
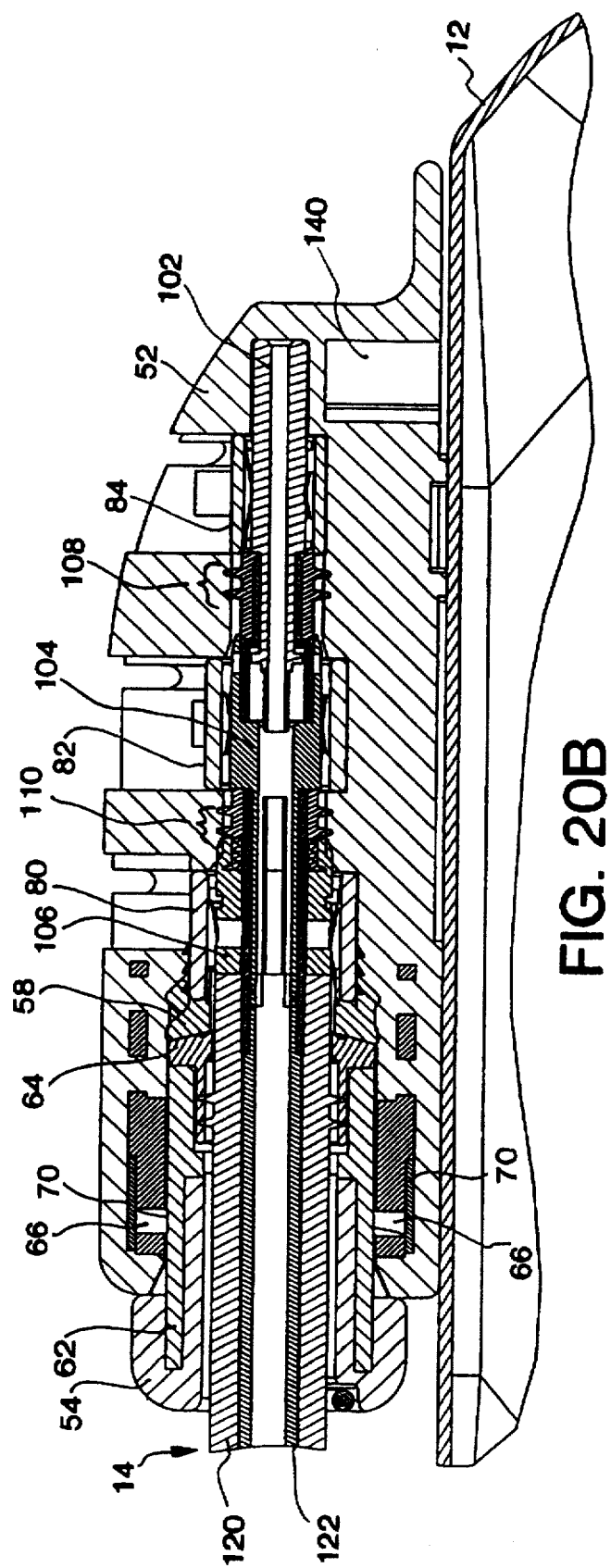

FIGS. 20a and 20b show lead 14 with its terminal assembly having been inserted into connector assembly 50; in FIG. 20a, rotating lever 54 is turned to its open position, while in FIG. 20b, lever 54 is in its closed position. Regarding insertion of lead 14 into connector assembly, in accordance with one aspect of the present invention this occurs in a "successive engagement" manner; i.e., the three electrodes 102, 104 and 106 on lead 14 are engaged one at a time by corresponding multibeam contact assembly 78, 76, 74 (see FIGS. 7a and 7b) as lead 14 is inserted into socket 56. As lead 14 is inserted into connector assembly 50, pin electrode 102 is first engaged in contact assembly 78. As lead 14 is pushed further into connector assembly, ring electrode 104 is engaged by contact assembly 76. Finally, ring electrode 106 is engaged by contact assembly 74. This successive engagement occurs as a result of the spacing of electrodes 102, 104, and 106 with respect to one another.

Engagement of each electrode by a corresponding contact assembly is preferably accompanied by the slight "click" or "bump" associated with conventional multibeam contacts, advantageously providing, separately for each electrode 102, 104, and 106, tactile feedback that the electrode has been engaged in connector assembly 50. The successive rather than simultaneous engagement of electrodes 102, 104, and 106 also advantageously minimizes the insertion force necessary to insert lead 14.

Once lead 14 has been fully inserted into socket 56, it is secured in connector assembly 50 by rotating lever 54 into the closed or locked position, shown in FIG. 20b. The J-groove engagement of lever 54 in main body portion 52 causes lever 54 to be drawn into main body portion 52 upon rotation into the closed position, thereby causing compression of sealing grommet 58 around lead body 14, as described above. When lever 54 is completely closed, it is held in place as a result of the overtravel and springback of J-groove 66, in accordance with conventional practice in the art.

The tapered geometries of thrust washer 64 and sealing grommet 58 not only facilitate the compression of sealing grommet 58 uniformly around lead body 14, but also function to facilitate subsequent release and withdrawal of lead 14 if lever 54 is returned to its open or unlocked position. To address the potential for adhesion between sealing grommet 58 and lead 14 over the long term, the geometries of thrust washer 64 and sealing grommet 58 are such that should any such adhesion occur, the taper of thrust washer 64 will tend to pull sealing grommet 58 away from lead 14 in a "snow plow" fashion as lead 14 is pulled out of connector assembly 50.

Those of ordinary skill in the art will recognize that the molded polyurethane from which main body portion 52 of connector assembly 50 is made is generally translucent. One alternative embodiment of the present invention takes advantage of this quality by providing a visual indicator of proper and complete insertion of lead 14 into connector assembly 50. In this alternative embodiment, a colored element 140, shown in FIGS. 7a, 7b, 20a and 20b, is molded into main body 52 of connector assembly 50 at a location immediately beneath where pin electrode 102 is situated when lead 14 is fully inserted into connector assembly 50. A shroud (not shown) may be disposed around the side of colored element 140 so that colored element 140 is only visible when looking down on connector assembly 50 from above, and then only when lead 14 has not been fully inserted into connector assembly 50. In this way, only when colored element 140 is not visible from above will the physician or clinician be assured that lead 14 has been fully inserted into connector assembly 50'.

Figure 21:
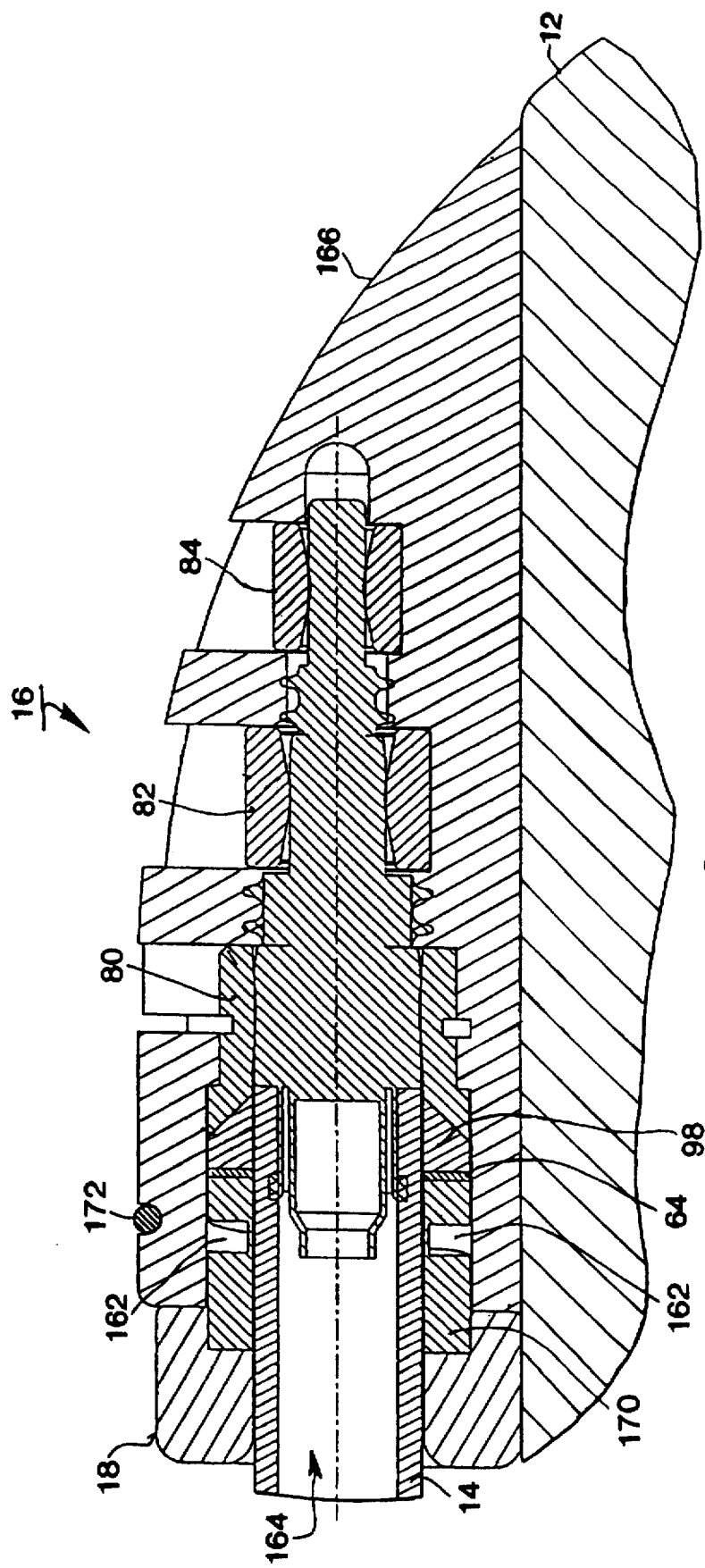
FIG. 21 is a side cross-sectional view of the connector assembly from FIGS. 1 and 2 with a lead similar to that described with reference to FIG. 8 inserted therein.

In FIG. 21, there is shown a more detailed cross-sectional view of the embodiment of the invention from FIGS. 1 and 2. As shown in FIG. 21, a J-groove 162 is formed on a plunger portion 170 of rotating lever 18. In this embodiment, cams (not shown) to be engaged within J-groove 162 protrude radially into socket 164. These cams may be the ends of a spring clip 172 which extend through main body portion 166 and into socket 164. The embodiment of FIG. 21 functions to seal around lead body 14 through compression of sealing grommet 58 by thrust washer 64 upon rotation of lever 168 to a closed position.

Figure 22:
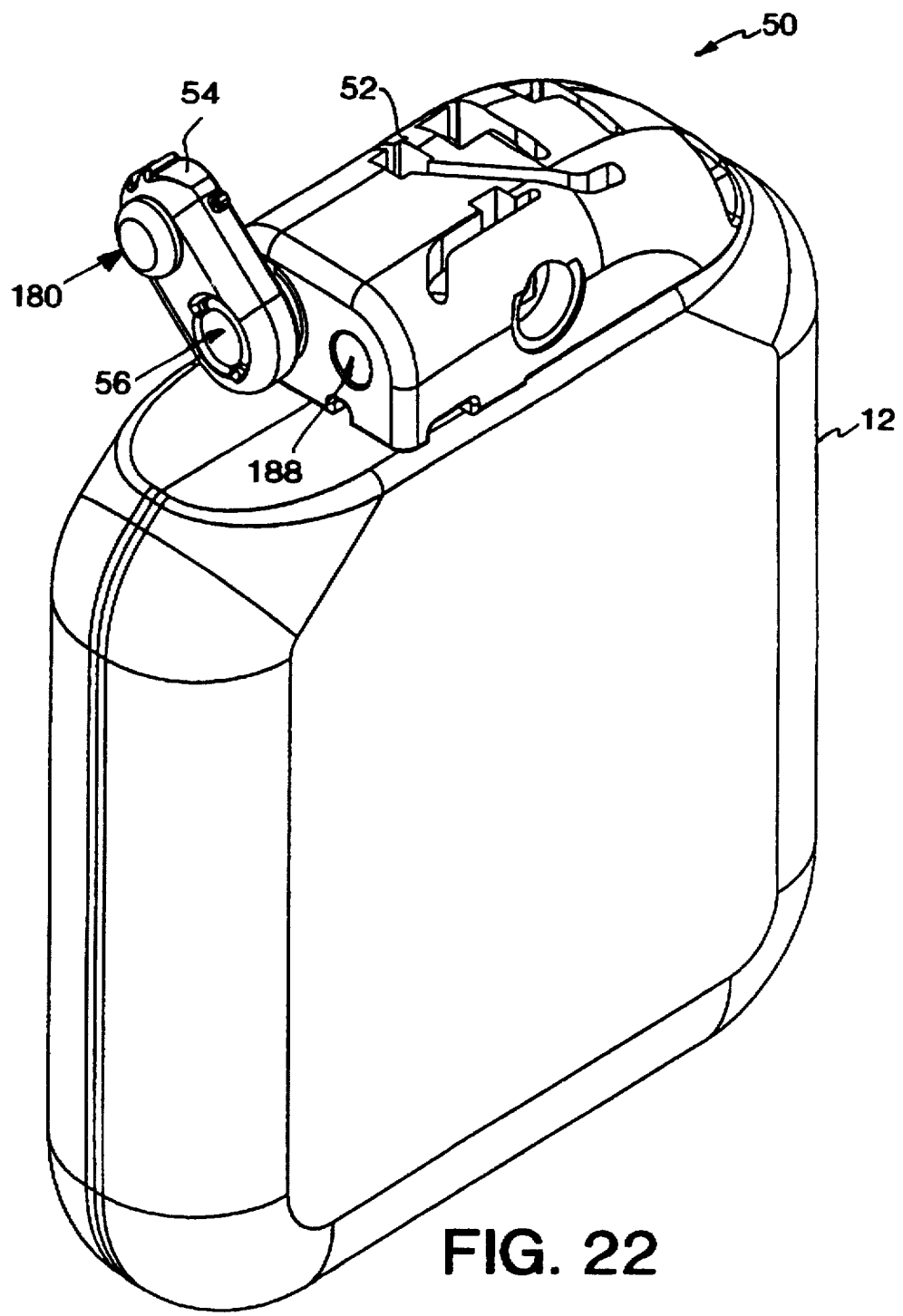
FIG. 22 is a perspective view of an implantable device system incorporating a connector assembly in accordance with the embodiment of FIGS. 7a and 7b, the connector assembly of FIG. 22 shown in an open position.
Figure 23A:
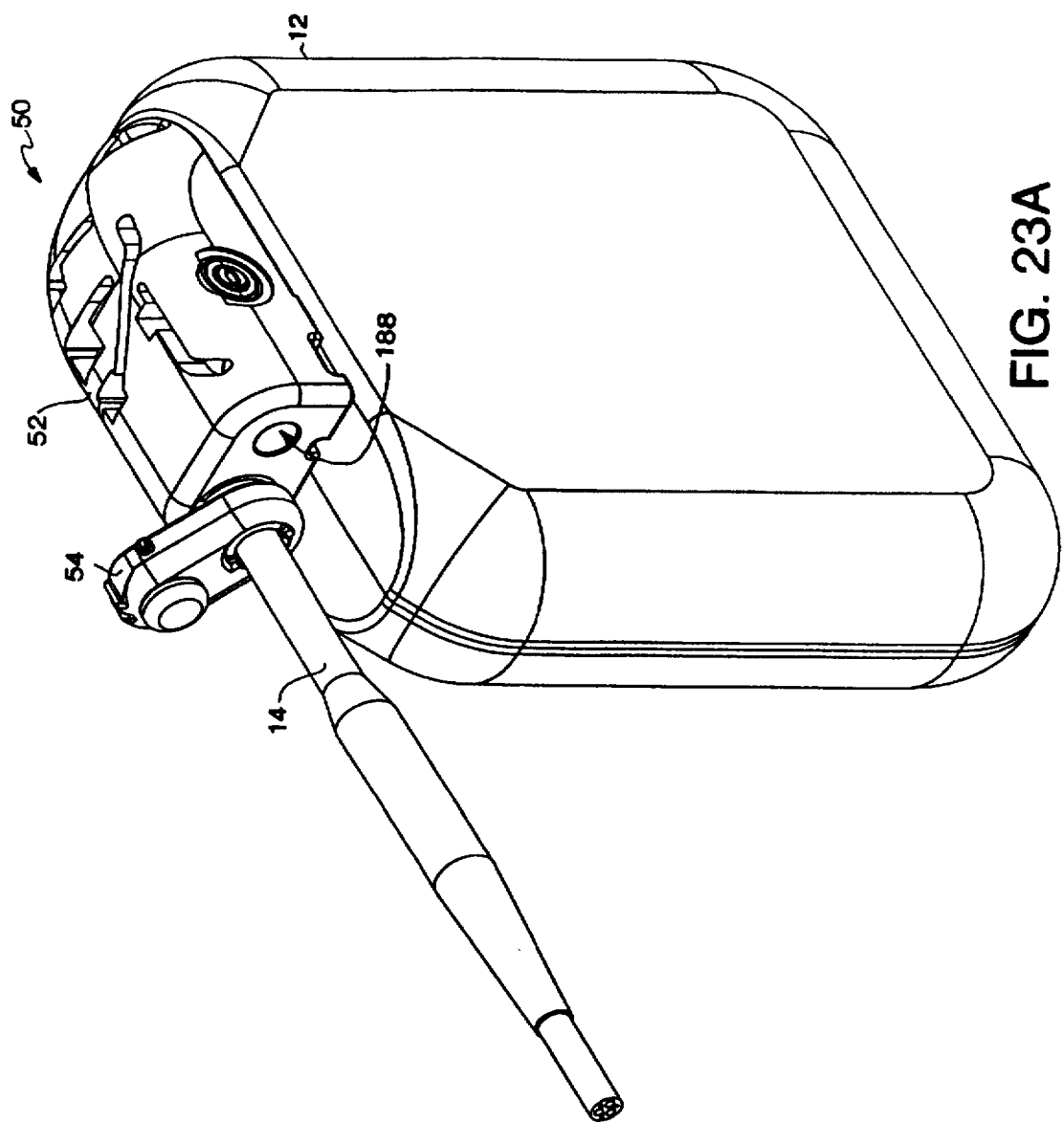
FIGS. 23a and 23b are perspective views of the implantable device system of FIG. 22 showing a lead inserted into the connector assembly thereof and showing the connector assembly in open and closed positions, respectively.
Figure 23B:
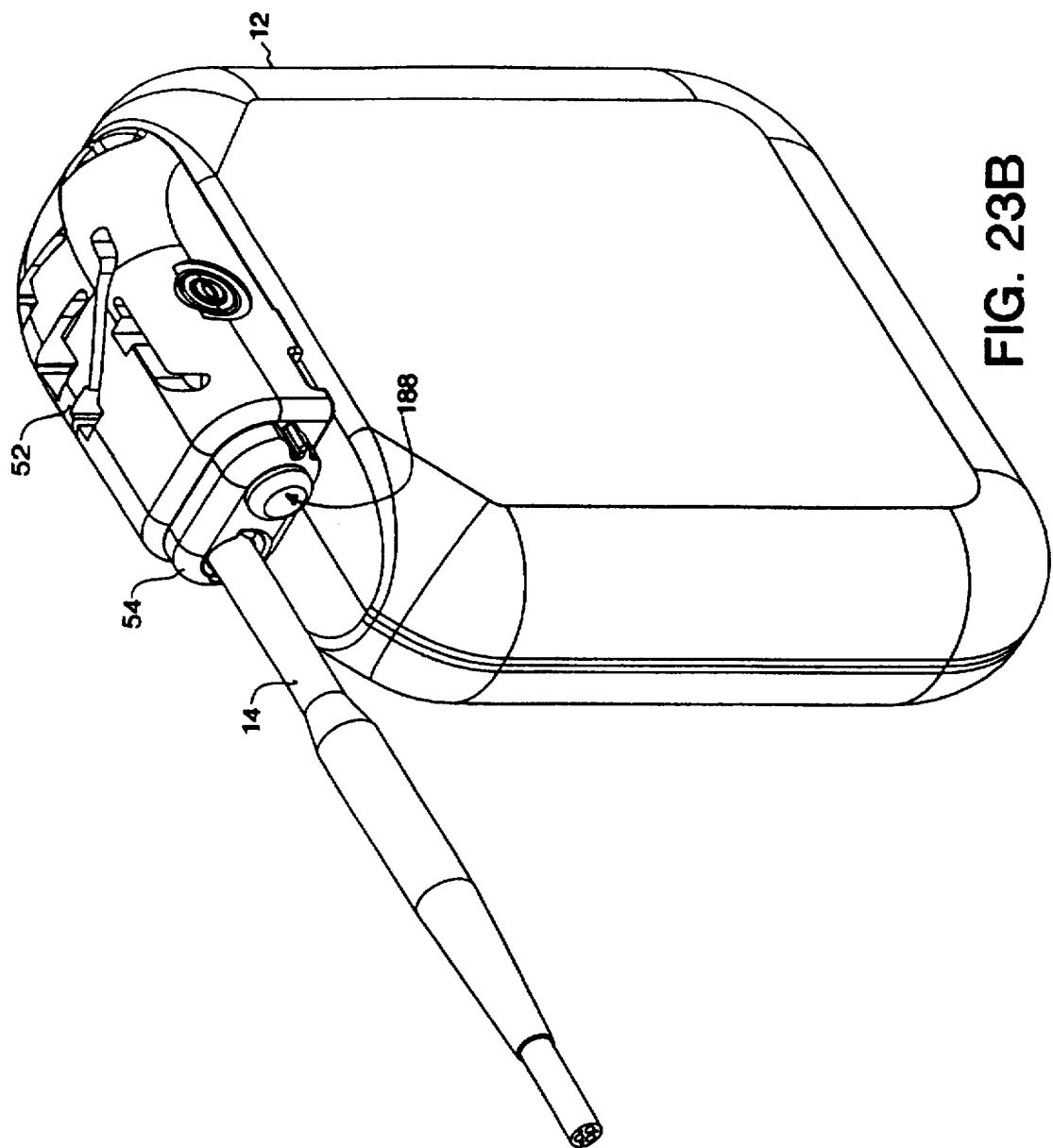
Figure 24:
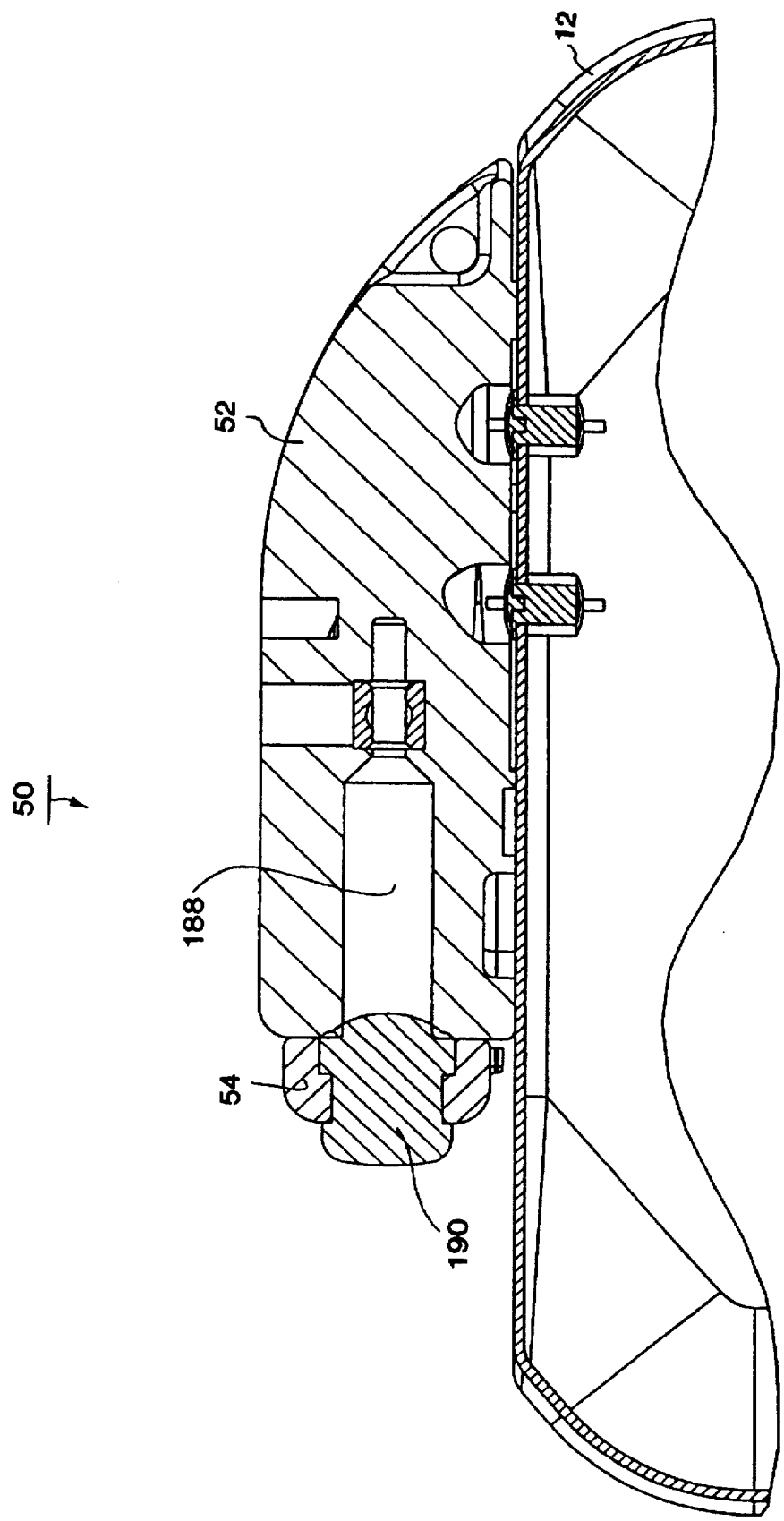
FIG. 24 is a side cross-sectional view of the connector assembly from the implantable device system of FIG. 22, showing the detail of a sealed supplemental port therein.

FIGS. 22–24 provide more detailed views of the embodiment from FIGS. 7a and 7b. The embodiment of FIGS. 7a, 7b, and 22–24 includes a connector assembly 50 comprising a main body portion 52 and a rotating lever 54. As shown in FIGS. 22, 23a, and 23b, main body 52 and rotating lever 54 together define two sockets 56 and 188 for receiving two separate leads therein. The first socket 186 is a tool-less sealing socket, i.e., a socket into which a lead is secured through rotation of lever 54 from the open position of FIG. 22 to the closed position of FIG. 23b. Sealing is accomplished through compression of a sealing grommet around lead 14, as previously described.

Socket 188 in the embodiment of FIGS. 7a, 7b, 22–24, on the other hand, is more conventional in nature, for example, one in which a lead is secured with set screws or the like. There are least two potential advantages to providing the two different sockets 56 and 188 in connector assembly 50. Connector assembly 50 may be advantageously provided for an implantable device requiring two separate leads, one of which being a lead having a conventional (e.g., set-screw) connection mechanism. Alternatively, connector assembly 50 may be advantageously provided to enable a pulse generator to be compatible with two different types of leads. For example, for new implants of a device, tool-less sealing socket 56 would be used. For implants in which an older device is being replaced, compatibility with the existing lead which may not need to be explanted would be desirable. In that case, conventional socket 188 could be used.

For situations in which a conventional connector is not necessary, there is preferably provided a means for sealing socket 188. As shown in FIG. 24, one method of accomplishing this is to provide a "dome-head" plug 190, which is inserted into the portion of socket 186 defined by rotating lever 184. Plug 190 is preferably made of silicone rubber or the like, and its domed configuration is such that when lever 184 is rotated into the closed position, a fluid-tight seal is made over the portion of socket 188 defined by main body portion 182.

Figure 25:
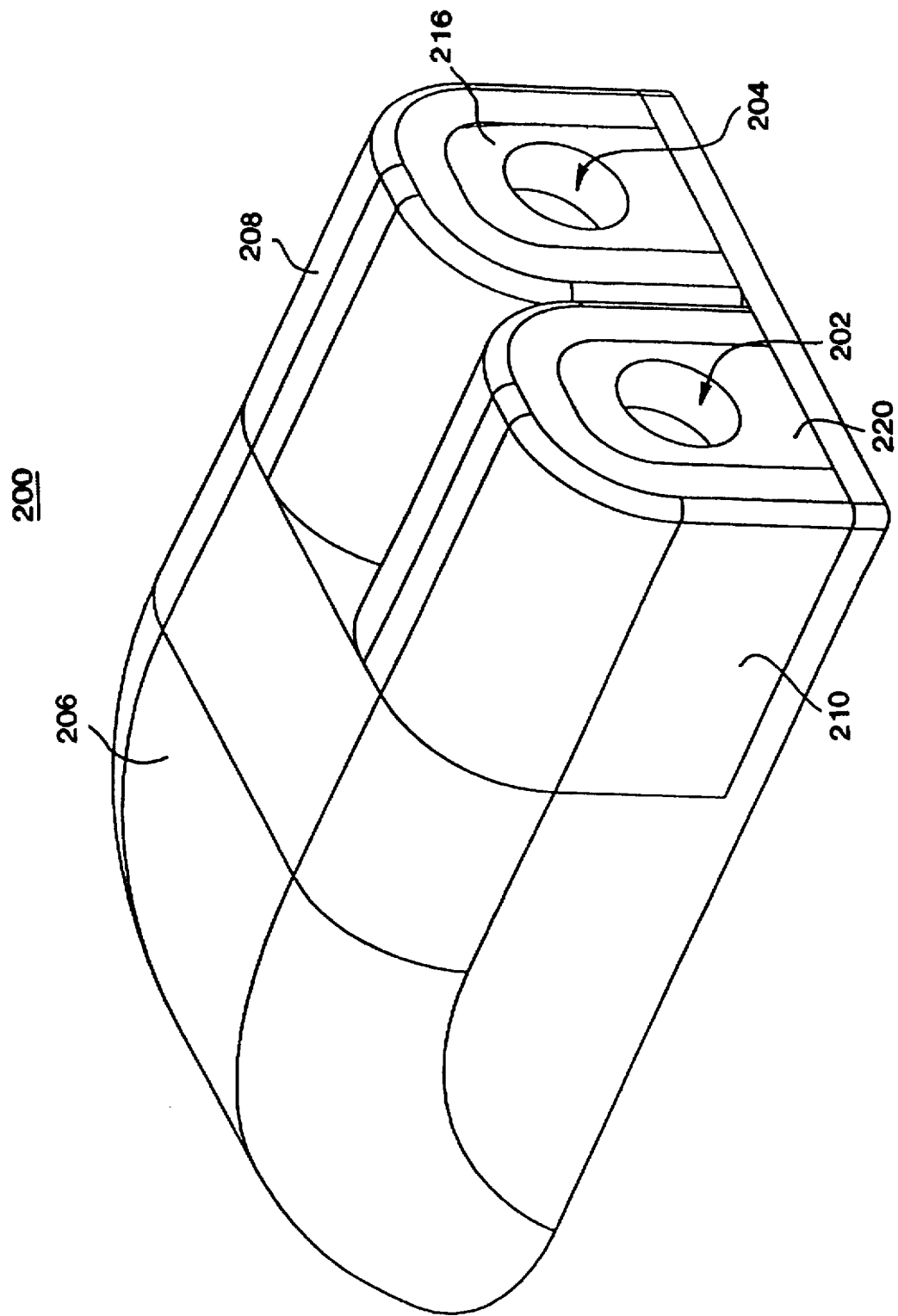
FIG. 25 is a perspective view of a connector assembly in accordance with still another embodiment of the invention.

Still another embodiment of the invention is shown in FIGS. 25–28. The embodiment of FIGS. 25–28 is a connector assembly 200 having two lead sockets 202 and 204 therein (although it is to be understood that an embodiment similar to that of FIGS. 25–28 but having only a single lead socket therein can be implemented). Each socket 202 and 204 is defined by a main body portion 206 and a compression slide 208 or 210. FIG. 25 shows compression slides 208 and 210 both in a closed position. Compression slides 208 and 210 are independently actuable into an open position, compression slide 210 being shown in its open position in FIG. 26.

Each compression slide 208 and 210, when moved from its open position to its closed position, causes an associated sealing grommet to be compressed around the body of a lead inserted into the corresponding socket 202 or 204, in much the same way as sealing grommet 58 is compressed in the embodiment of FIGS. 6–20b.

Figure 26:
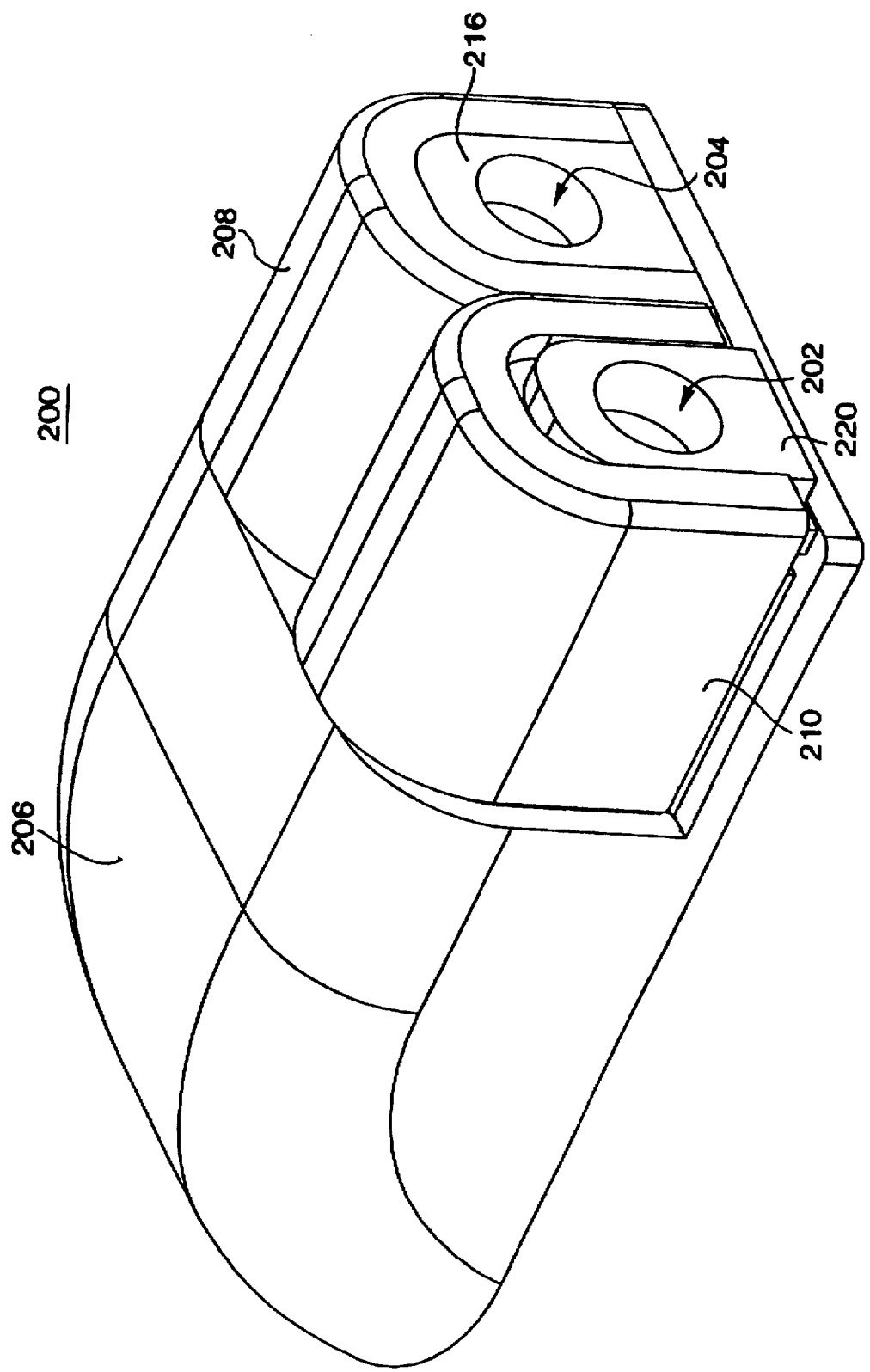
FIG. 26 is another perspective view of the connector assembly from FIG. 25.
Figure 27:
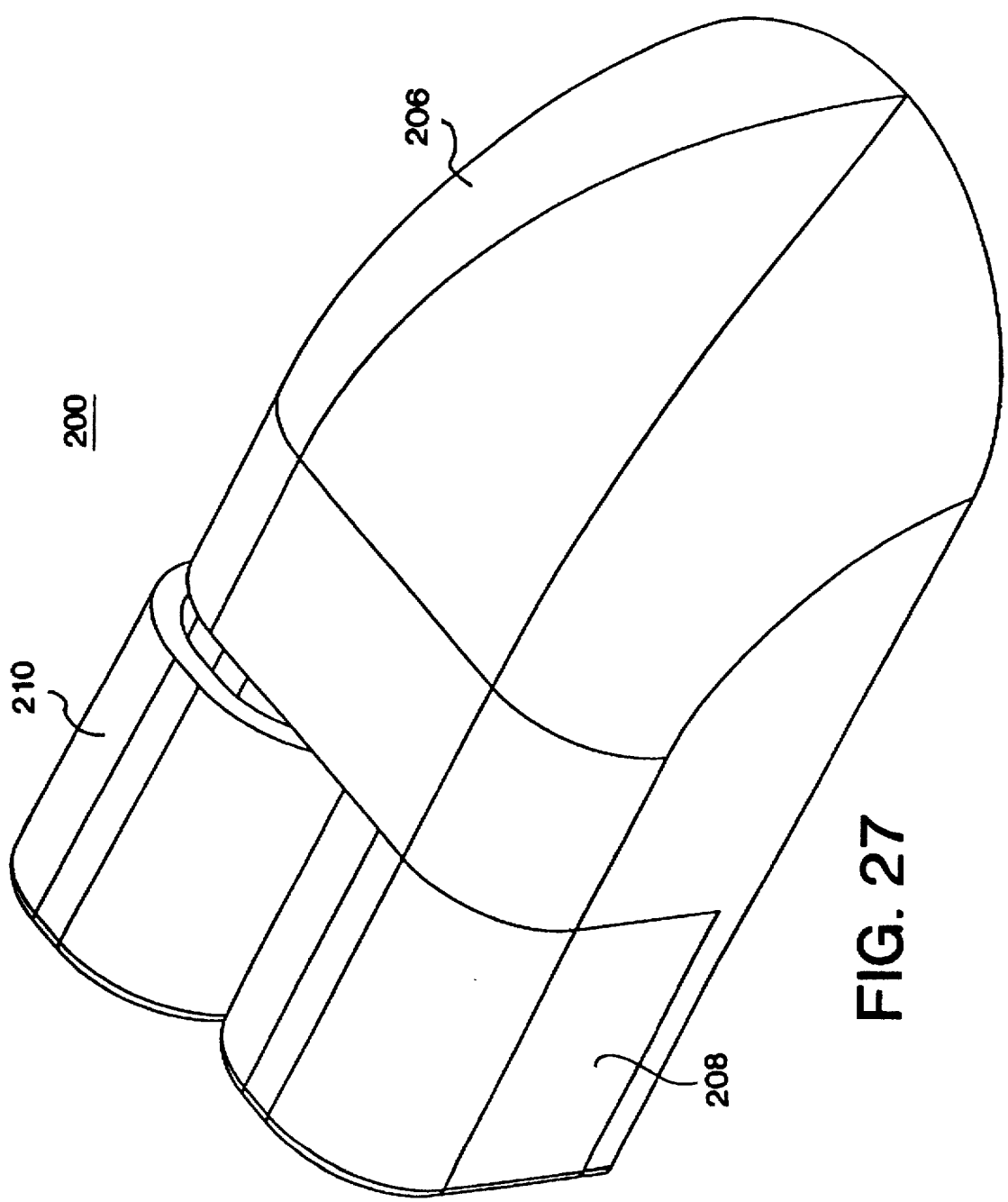
FIG. 27 is still another perspective view of the connector assembly from FIG. 25.
Figure 28:
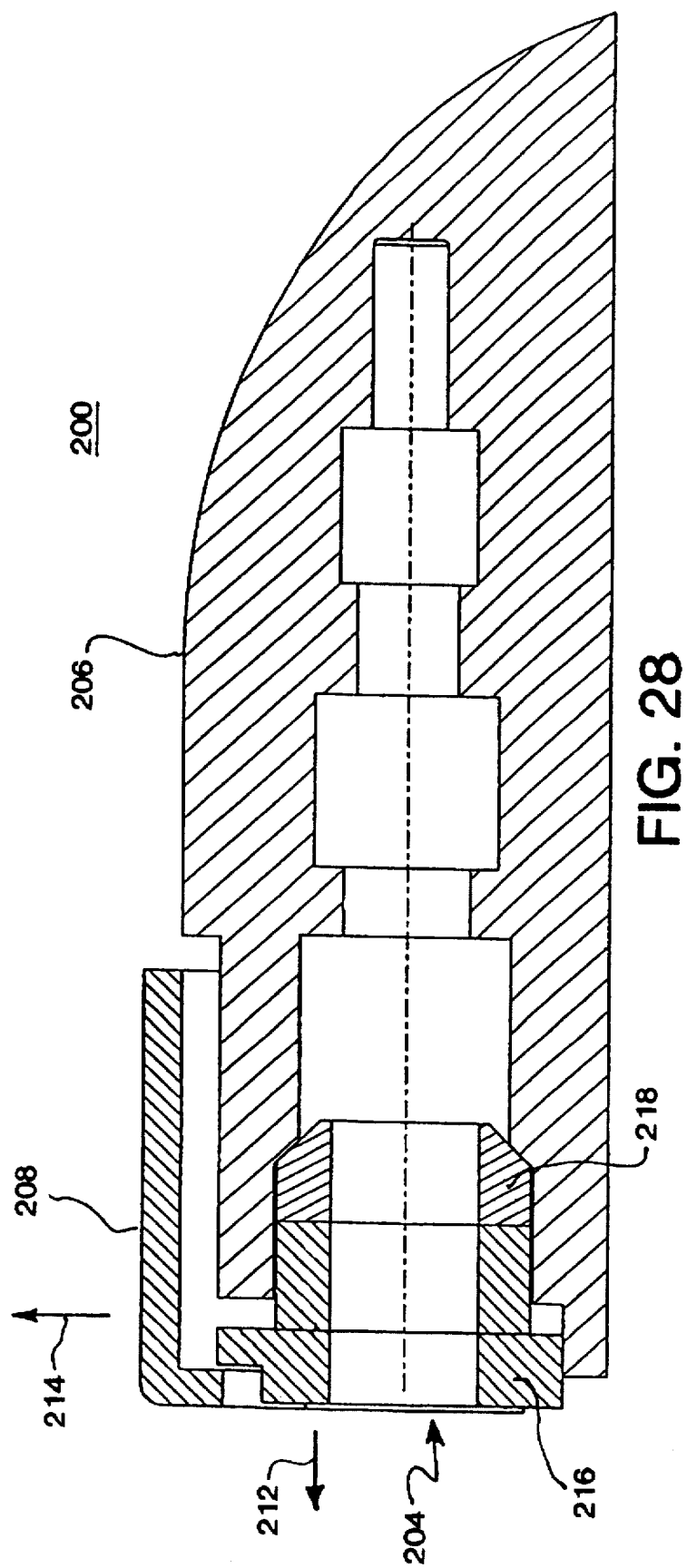
FIG. 28 is a side cross-sectional view of the connector assembly from FIG. 25.

FIG. 28 shows a side cross-sectional view of socket 204 in its open position. From FIG. 28 it can be seen that slide 208 travels both forward and up when moved from its closed position to its open position (i.e., in the direction of arrows 212 and 214), and travels both backward and down when moved from its open position to its closed position. As a result, when slide 208 is closed, an associated thrust element 216 is pushed inward, compressing a sealing grommet 218 around the body of a lead (not shown) inserted into socket 204. (A corresponding thrust element 220 is associated with slide 210, as shown in FIGS. 25 and 26.

Figure 29:
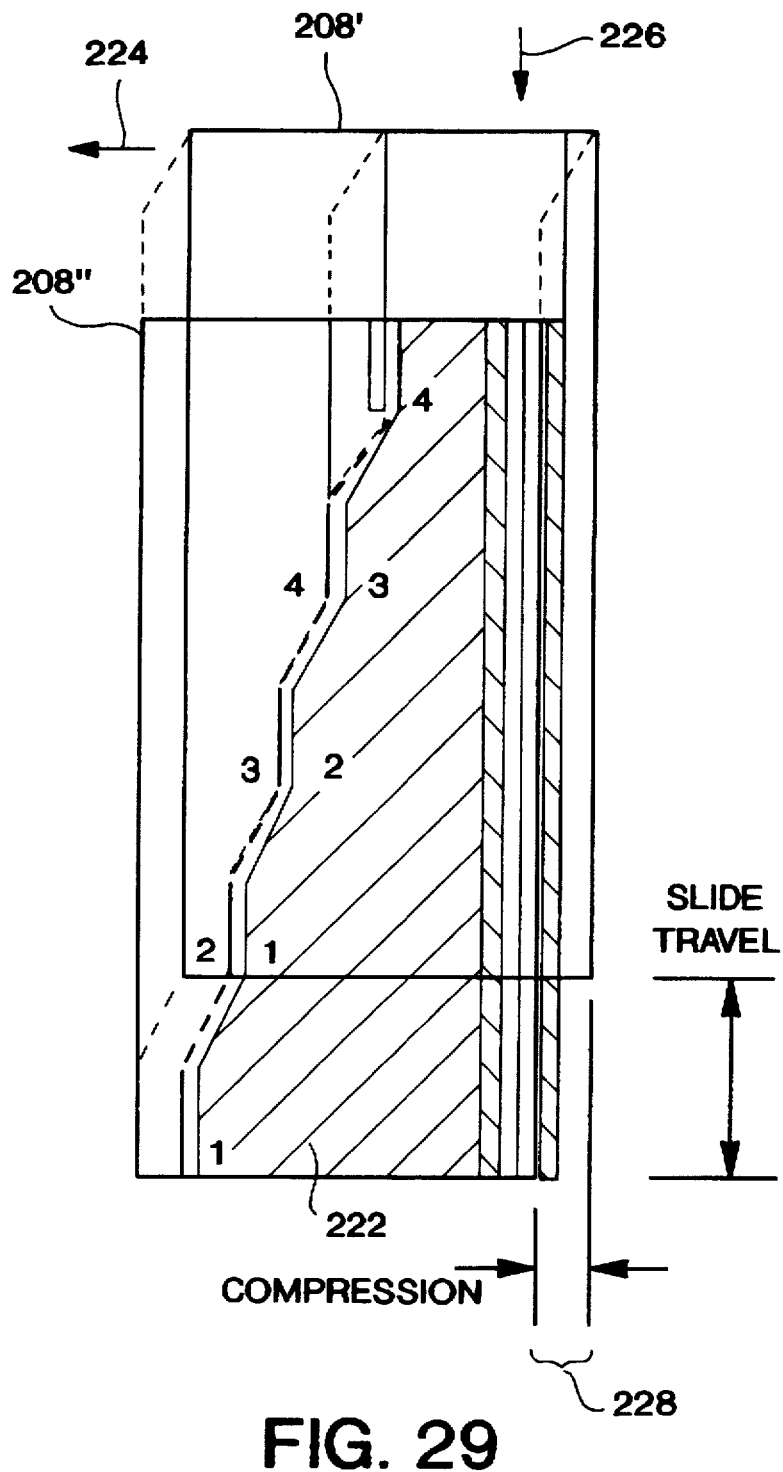
FIG. 29 is a diagram illustrating the manner in which a slide portion of the connector assembly of FIG. 25 is moved between open and closed positions.

FIG. 29 illustrates conceptually how the movement of slide 208 occurs (it being understood that the movement of slide 210 occurs in an identical manner). Movement of slide 208 is dictated by complementary stepped-ramp bosses which protrude from main body portion 206 and slide 208. A stepped-ramp boss on main body portion 206 is represented by shaded area 222 in FIG. 29. A complementary stepped-ramp boss on the wall of slide 208 causes inward travel (arrow 224) of slide 208 when downward force (arrow 226) is applied to move slide 208 from its open position (designated by reference numeral 208' in FIG. 29) to its closed position (designated by reference numeral 208" in FIG. 29). The extent of compression achieved through movement from position 208' to position 208" is represented by reference numeral 228 in FIG. 29.

From the foregoing detailed description of specific embodiments of the invention, it should be apparent that a method and apparatus for providing a tool-less connector assembly for implantable devices has been disclosed. Although numerous specific details regarding the various embodiments of the invention have been provided, it is to be understood that this has been done for the purposes of illustrating various aspects of the invention, and is not intended to be limiting with respect to the scope of the invention. It is believed that numerous alterations, substitutions, and/or modifications, including but not limited to those specifically noted herein, may be made to the disclosed embodiments without departing from the spirit and scope of the invention as defined in the following claims:

What is claimed is:

1. A connector assembly for an implantable medical device, said connector assembly comprising:

a main connector body defining first and second sockets separated from one another in said connector body each of said first and second sockets having a conductive terminal therein and having an open end for receiving a proximal connector portion of an implantable electrical lead and;

an annular sealing grommet disposed within said main connector body and surrounding said first socket;

a locking lever, rotatably coupled to a front face portion of said main connector body and having a first bore aligned with said open end of said first socket and a second bore, said lever being rotatable from a first, open position to a second, closed position;

wherein rotation of said lever from said first position to said second position compresses said sealing grommet around said lead's circumference to effectuate a seal around said lead and wherein said second bore of said lever is aligned with the open end of said second socket when said lever is in said second position.

2. A connector assembly in accordance with claim 1, wherein said locking lever defines a plurality of cams adapted to be engaged in a J-groove formed in said main connector body to effectuate said rotatable coupling between said locking lever and said main connector body.

3. A connector assembly for an implantable medical device, said connector assembly comprising:

a main connector body defining first and second sockets separated from one another in said connector body, each of said first and second sockets having a conductive terminal therein and having an open end for receiving a proximal connector portion of an implantable electrical lead;

an annular sealing grommet disposed within said main connector body and surrounding said first socket;

a locking lever, rotatably coupled to a front face portion of said main connector body and having a first bore aligned with said open end of said first socket and having a seal located thereon, said lever being rotatable from a first, open position to a second, closed position;

wherein rotation of said lever from said first position to said second position compresses said sealing grommet around said lead's circumference to effectuate a seal around said lead and wherein said seal on said lever seals the open end of said second socket when said lever is in said second position.

4. A connector assembly according to claim 3 wherein said lever is provided with a second bore which is aligned with said second socket when said lever is in said second position and wherein said seal is removably mounted in said second bore.

* * * * *